US012702808B2

(12) United States Patent
Yoshimoto et al.

(10) Patent No.: US 12,702,808 B2
(45) Date of Patent: Aug. 11, 2026

(54) MEDICAL ELONGATED BODY AND MEDICAL ELONGATED BODY SET

(71) Applicant: TERUMO KABUSHIKI KAISHA, Tokyo (JP)

(72) Inventors: Shosei Yoshimoto, Odawara (JP); Ryo Okamura, Fujinomiya (JP)

(73) Assignee: TokyoTERUMO KABUSHIKI KAISHA (JP)

( * ) Notice: Subject to any disclaimer, the term of this patent is extended or adjusted under 35 U.S.C. 154(b) by 769 days.

(21) Appl. No.: 18/180,916

(22) Filed: Mar. 9, 2023

(65) Prior Publication Data

US 2023/0218877 A1 Jul. 13, 2023

Related U.S. Application Data

(63) Continuation of application No. PCT/JP2021/033114, filed on Sep. 9, 2021.

(30) Foreign Application Priority Data

Sep. 10, 2020 (JP) ................................ 2020-152098

(51) Int. Cl.

| | |
|---|---|
| ***A61M 39/02*** | (2006.01) |
| ***A61M 25/00*** | (2006.01) |
| ***A61M 25/06*** | (2006.01) |

(52) U.S. Cl.

CPC .... *A61M 39/0247* (2013.01); *A61M 25/0097* (2013.01); *A61M 25/0662* (2013.01);

(Continued)

(58) Field of Classification Search

CPC .......... A61M 25/0662; A61M 25/0097; A61M 2025/0057; A61M 2025/0681;

(Continued)

(56) References Cited

U.S. PATENT DOCUMENTS 4,610,665 A * 9/1986 Matsumoto ....... A61M 39/0606 604/167.04
4,673,393 A * 6/1987 Suzuki ............. A61M 39/0606 604/167.04

(Continued)

FOREIGN PATENT DOCUMENTS

FR 2689402 A1 * 10/1993 ........ A61M 25/0662
JP 2010233682 A 10/2010

(Continued)

OTHER PUBLICATIONS

English Translations of the International Search Report (Form PCT/ISA/210) and the Written Opinion of the International Searching Authority (Form PCT/ISA/237) issued Nov. 9, 2021, by the Japan Patent Office in corresponding International Application No. PCT/JP2021/033114. (5 pages).

(Continued)

*Primary Examiner* — Wesley G Harris

(74) *Attorney, Agent, or Firm* — BUCHANAN INGERSOLL & ROONEY PC

(57) ABSTRACT

An elongated medical catheter body, which may constitute an introducer sheath includes: a catheter body; a hub fixed to a proximal portion of the catheter body; and a support member connected to the hub and configured to cover of the proximal portion of the catheter body. The catheter body includes a groove on the outer surface of the catheter body, and the support member is disposed so as to partially cover the groove. The support member includes a drug part having a drug solution, and a partition wall portion is located between the drug part and the groove, and the partition wall portion is configured to make the drug part communicate with the groove portion upon being broken by pressure or by causing damage.

20 Claims, 14 Drawing Sheets

(52) U.S. Cl.
CPC ............... *A61M 2025/0057* (2013.01); *A61M 2025/0681* (2013.01); *A61M 2039/0205* (2013.01); *A61M 2039/0258* (2013.01)

(58) Field of Classification Search
CPC ...... A61M 39/0247; A61M 2039/0205; A61M 2039/0258; A61B 17/0057; A61B 17/3417; A61B 17/3415
See application file for complete search history.

(56) References Cited

U.S. PATENT DOCUMENTS

| | | | | | |
|---|---|---|---|---|---|
| 5,054,500 | A * | 10/1991 | Littleford | A61M 25/0662 | 600/585 |
| 5,405,334 | A * | 4/1995 | Roth | A61J 15/0092 | 604/264 |
| 5,484,425 | A * | 1/1996 | Fischell | A61M 25/005 | 604/528 |
| 5,533,986 | A * | 7/1996 | Mottola | A61M 25/0075 | 604/264 |
| 2004/0210194 | A1 * | 10/2004 | Bonnette | A61B 17/22 | 604/167.06 |
| 2006/0004408 | A1 * | 1/2006 | Morris | A61L 27/3645 | 606/215 |
| 2009/0306606 | A1 * | 12/2009 | Lancette | A61M 39/0208 | 604/513 |
| 2018/0056036 | A1 | 3/2018 | Wada | | |
| 2019/0192826 | A1 | 6/2019 | Wada | | |
| 2021/0000538 | A1 * | 1/2021 | Otsubo | A61M 25/005 | |
| 2022/0016397 | A1 * | 1/2022 | Wilson | A61M 25/09 | |

FOREIGN PATENT DOCUMENTS

| | | | | |
|---|---|---|---|---|
| JP | 2018033792 | A | 3/2018 | |
| WO | 2012132774 | A1 | 10/2012 | |
| WO | 2018043427 | A1 | 3/2018 | |
| WO | WO-2022045323 | A1 * | 3/2022 | A61B 17/34 |

OTHER PUBLICATIONS

International Search Report (PCT/ISA/210) with translation and Written Opinion (PCT/ISA/237) mailed on Nov. 9, 2021, by the Japanese Patent Office as the International Searching Authority for International Application No. PCT/JP2021/033114. (8 pages).

* cited by examiner 100b
134
170a
132a
131a
180a
130b
112
160

MEDICAL ELONGATED BODY AND MEDICAL ELONGATED BODY SET

CROSS-REFERENCES TO RELATED APPLICATIONS

This application is a continuation of International Patent Application No. PCT/JP2021/033114 filed on Sep. 9, 2021, which claims priority to Japanese Patent Application No. 2020-152098 filed on Sep. 10, 2020, the entire content of both of which is incorporated herein by reference.

TECHNOLOGICAL FIELD

The present invention generally relates to a medical elongated body used for an introducer assembly as a medical instrument and a medical elongated body set.

BACKGROUND DISCUSSION

In the medical field, procedures for percutaneously introducing various catheters and the like into living bodies are performed. In such procedures, since various catheters and the like are percutaneously inserted into the living bodies, an introducer sheath is used as a medical instrument connecting the inside and outside of the living bodies. For example, the introducer sheath includes a catheter body percutaneously inserted into a biological lumen such as a blood vessel, and a hub connected to a proximal side of the catheter body.

In a procedure using the introducer sheath, an operator percutaneously inserts the catheter body of the introducer sheath into the blood vessel through a puncture site (perforation) formed on the limb or the like of the patient in a state in which a dilator is inserted into the introducer sheath. The operator withdraws the dilator from the introducer sheath in a state in which the catheter body is inserted into the blood vessel. Accordingly, the introducer sheath forms an access path connecting the inside of the living body with the outside of the living body in a state in which the catheter body is percutaneously inserted into the biological lumen. After withdrawing the dilator from the introducer sheath, the operator can insert a guide wire, various catheters, or the like into the blood vessel through the lumen of the catheter body.

After inserting the guide wire or various catheters into the blood vessel and performing treatment of a lesion site in the blood vessel, the operator withdraws the introducer sheath from the blood vessel, and performs hemostasis at the puncture site into which the introducer sheath is inserted. Typically, when performing hemostasis at the puncture site, the operator compresses the puncture site by using a hemostatic instrument or the like for compressing the puncture site.

However, hemostasis at the puncture site requires compressing the puncture site for a long period of time. In addition, it is necessary for the operator to operate the hemostatic instrument such that the occlusion of the artery or the like does not occur even in the long-time hemostatic treatment when the compression force of the hemostatic instrument or the like compressing the puncture site is reduced over time. Therefore, there is a demand for a technique capable of stopping bleeding in a short time in order to lessen a patient's physical burden related to hemostasis at the puncture site and simplify the hemostatic treatment of the operator.

In recent years, as described in International Publication (WO) No. 2018/043427, in order to shorten the time required for hemostasis at the puncture site of the patient and lessen the patient's physical burden, proposals have been made to promote hemostasis at the puncture site by disposing a hemostatic agent capable of treating a wound site on the outer surface of the catheter body of the introducer sheath.

SUMMARY

In the introducer sheath described in International Publication (WO) No. 2018/043427, the hemostatic agent is disposed on the outer surface of the catheter body. Furthermore, the introducer sheath described in International Publication (WO) No. 2018/043427 prevents the hemostatic agent from falling off from the catheter body before the hemostatic agent is introduced into the puncture site, and prevents the hemostatic agent from being lost (removed) due to abrasion caused when the hemostatic agent comes into contact with fingers of an operator or a surrounding article, and thus the hemostatic agent is covered by a cover member or a strain relief.

However, in the introducer sheath of International Publication (WO) No. 2018/043427, when the hemostatic agent is introduced into the puncture site, it is necessary to remove the cover member covering the hemostatic agent and the strain relief to expose the hemostatic agent on the surface of the catheter body. In addition, in the introducer sheath of International Publication (WO) No. 2018/043427, after the hemostatic agent is exposed on the surface of the catheter body, it is necessary to further press the catheter body into the blood vessel such that the hemostatic agent is disposed at the puncture site. Therefore, when disposing the hemostatic agent at the puncture site by using the introducer sheath of International Publication (WO) No. 2018/043427, the operator needs to remove the cover member or the strain relief so as not to come into contact with the hemostatic agent, and then carefully move the catheter body so as not to come into contact with the hemostatic agent. Accordingly, the introducer sheath disclosed in International Publication (WO) No. 2018/043427 is susceptible of improvements in terms of structure when the hemostatic agent is administered to the puncture site in consideration of operability of the operator.

The disclosed medical elongated body is capable of shortening the time required for hemostasis at a wound site such as a puncture site and lessening the patient's physical burden by administering a drug such as a hemostatic agent to the wound site with a simple operation.

According to an embodiment, there is a medical elongated body including a catheter body, a hub fixed to a proximal portion of the catheter body, and a support member connected to the hub and configured to cover a part of a proximal side of the catheter body. The catheter body includes a groove portion on the outer surface of the catheter body, and the support member is disposed so as to partially cover the groove portion. The support member includes a drug part having a drug solution and a partition wall portion located between the drug part and the groove portion, and the partition wall portion is configured to make the drug part communicate with the groove portion in a state of being broken by pressure or by causing damage. Furthermore, there is a medical elongated body set including the medical elongated body and a needle member having a sharp distal portion configured to be capable of breaking the partition wall portion. In the medical elongated body set, the support member of the medical elongated body includes a marker portion serving as a mark when the needle member is inserted in a circumferential direction of the catheter body.

In the medical elongated body and medical elongated body set, it is possible to administer the drug solution to the wound site via the groove portion of the catheter body with a simple operation, and it is possible to shorten a time required for hemostasis at the wound site of the patient and lessen the burden on the patient and the operator. That is, in the medical elongated body, the catheter body is percutaneously inserted into the blood vessel from the puncture site, and the partition wall portion of the support member is broken with a simple operation such as compression of the support member in a state in which the groove portion of the catheter body is inserted into the wound site (puncture site). Therefore, the drug solution of the drug part of the support member can be administered to the wound site via the groove portion of the catheter body. Furthermore, since the operation of the operator administering the drug solution to the wound site by using the medical elongated body is only the operation of breaking the partition wall portion, the drug solution can be administered to the wound site without moving the catheter body placed in the wound site. In addition, since the medical elongated body is disposed such that the support member partially covers the groove portion, it is possible to prevent the operator from touching the drug solution when the operator administers the drug solution to the wound site. Therefore, the operator can administer the drug solution to the wound site with a simple operation, and the hemostasis time at the wound site can be shortened by the hemostatic action of the drug solution. In particular, in a case of being used in combination with the hemostatic instrument for stopping bleeding by compressing the wound site such as the puncture site, the hemostasis time can be shortened by the drug solution. Therefore, it is possible to reduce the labor and time for the operator's decompression operation and reduce the risk of artery occlusion and the like. Moreover, since the medical elongated body includes the partition wall portion between the drug part and the groove portion, after the catheter body is percutaneously inserted into the blood vessel from the wound site, it is possible to prevent the drug solution from being administered to the wound site in a state before the partition wall portion is broken. Therefore, the operator can break the partition wall portion of the support member by giving pressure or causing damage and administer the drug solution to the wound site at any timing.

According to another aspect, a medical elongated body comprises: an elongated catheter body extending in a longitudinal direction from a proximal end of the elongated catheter body to a distal end of the elongated catheter body, with the elongated catheter body possessing a proximal portion positioned closer to the proximal end of the elongated catheter body than the distal end of the elongated catheter body, and the elongated catheter body also possessing an outer surface; and a hub fixed to the proximal portion of the elongated catheter body, with the hub possessing a proximal end and a distal end; a support member connected to the hub, surrounding a portion of the elongated catheter body located distal of the distal end of the hub, and possessing an outer surface. The elongated catheter body includes a groove on the outer surface of the elongated catheter body, and an axially extending portion of the support member overlies one portion of the groove, while another portion of the groove is uncovered and exposed to outside the elongated medical body, wherein the other portion of the groove is distal of the one portion of the groove. A drug solution is contained in an enclosed part that is located radially inwardly of the outer surface of the support member and radially outwardly of the outer surface of the elongated catheter body, and the enclosed part includes a partition wall. The enclosed part encloses the drug solution in a way that prevents the drug solution from flowing into the groove. The partition wall portion is breakable by contact with an object so that the drug solution in the enclosed part is free to flow to the groove.

Another aspect involves a treatment method comprising: percutaneously inserting a medical elongated body through a wound site and into a biological lumen. The medical elongated body comprises: a catheter body extending in a longitudinal direction and possessing a proximal portion and an outer surface, with the catheter body including a groove on the outer surface of the catheter body; a hub fixed to the proximal portion of the catheter body; a support member connected to the hub and covering a part of the catheter body, with the support member also covering a part of the groove; and a drug solution in an enclosed part that prevents the drug solution in the enclosed part from flowing into the groove. The enclosed part is positioned radially inwardly of an outer surface of the support member and is positioned between the proximal and distal ends of the support member relative to the longitudinal direction, and the enclosed part includes a partition wall. The treatment method also includes positioning the medical elongated body so that a portion of the groove faces the wound site, and breaking the partition wall so that the drug solution flows into the groove and is brought into contact with the wound site by way of the portion of the groove facing the wound site.

BRIEF DESCRIPTION OF THE DRAWINGS

FIG. 4A is a view illustrating a state of being punctured with an introduction needle, FIG. 4B is a view illustrating a state in which a guide wire is inserted into a biological lumen, FIG. 4C is a view illustrating a state in which a guide wire is placed in the biological lumen, FIGS. 4D and 4E are views illustrating a state of being punctured with an introducer assembly, and FIG. 4F is a view illustrating a state in which the medical elongated body is placed in the biological lumen.

FIG. 8 is a view illustrating a portion of a medical elongated body set according to the modification example of the support member and needle member, the portion corresponding to the left side of the center line of FIG. 3.

FIG. 9 is a view illustrating a portion of a medical elongated body set according to the modification example of the support member and needle member, the portion corresponding to the left side of the center line of FIG. 3.

FIG. 10A is a view illustrating a portion corresponding to the left side of the center line of FIG. 3, and FIG. 10B is a view illustrating a part of the support member of FIG. 10A in a transparent manner and illustrating a drug part and the needle member when viewed from an outer side of the catheter body in a radial direction.

DETAILED DESCRIPTION

Figure 1:
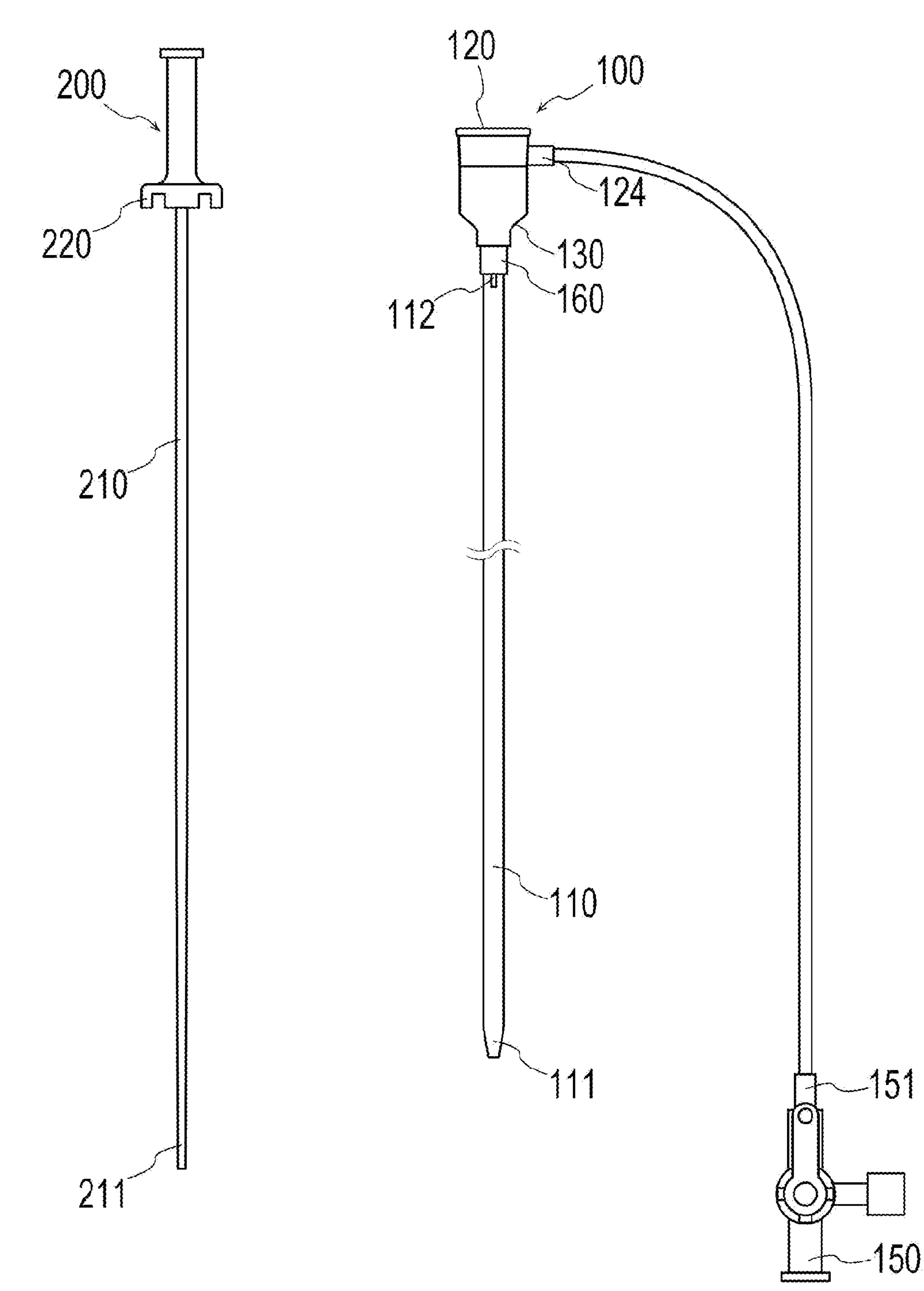
FIG. 1 is a view illustrating a medical elongated body according to a first embodiment.

Hereinafter, embodiments of the medical elongated body and medical elongated body set will be described in detail with reference to the drawings. The embodiments illustrated herein are illustrated to embody the technical idea of the disclosure here, and do not limit the present invention. Furthermore, other embodiments, examples, operation techniques, and the like that can be implemented by those skilled in the art without departing from the spirit t of the present invention are all included in the scope of the present invention and included in the invention described in the claims and the scope of equivalents thereof.

For convenience of illustration and ease of understanding, the dimensions, scale, shape, aspect ratio and the like in the drawings may be exaggerated or different from actuality/reality.

In the following description, the ordinal numerals such as "first" and "second" are used for convenience and do not define any order unless otherwise specified.

A medical elongated body according to an embodiment is applied to introducer sheaths 100, 100*a*, 100*b*, 100*c*, 100*d*, 100*e*, 100*f*, and 100*g* constituting an introducer assembly 10, but the application of the disclosed medical elongate body is not particularly limited. Furthermore, the contents of specific procedures, treatment procedures, and the like using the medical elongated body according are also representative examples, and do not limit the present invention.

First Embodiment

Hereinafter, a medical elongated body according to the first embodiment will be described with reference to the drawings. In the first embodiment, it is assumed that the medical elongated body is applied to an introducer sheath 100 constituting the introducer assembly 10.

Figure 2:
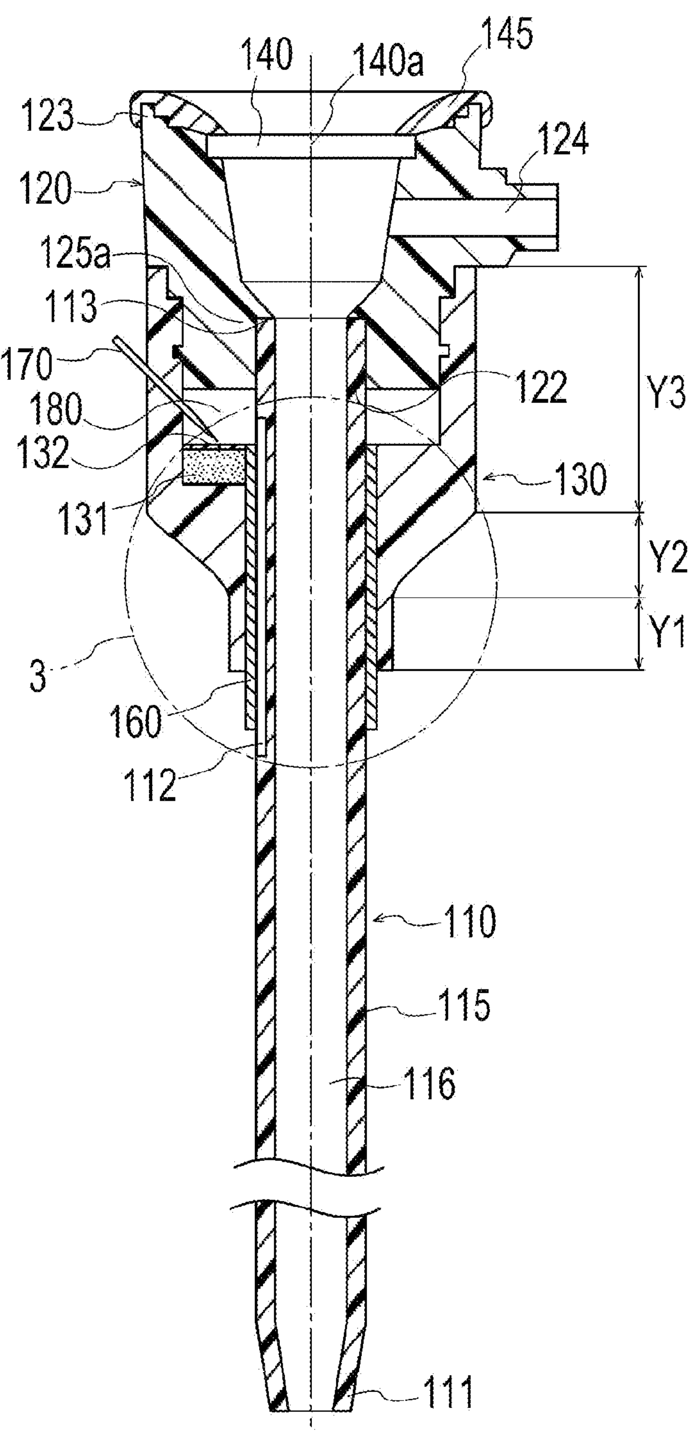
FIG. 2 is a cross-sectional view of a medical elongated body according to the first embodiment.
Figure 3:
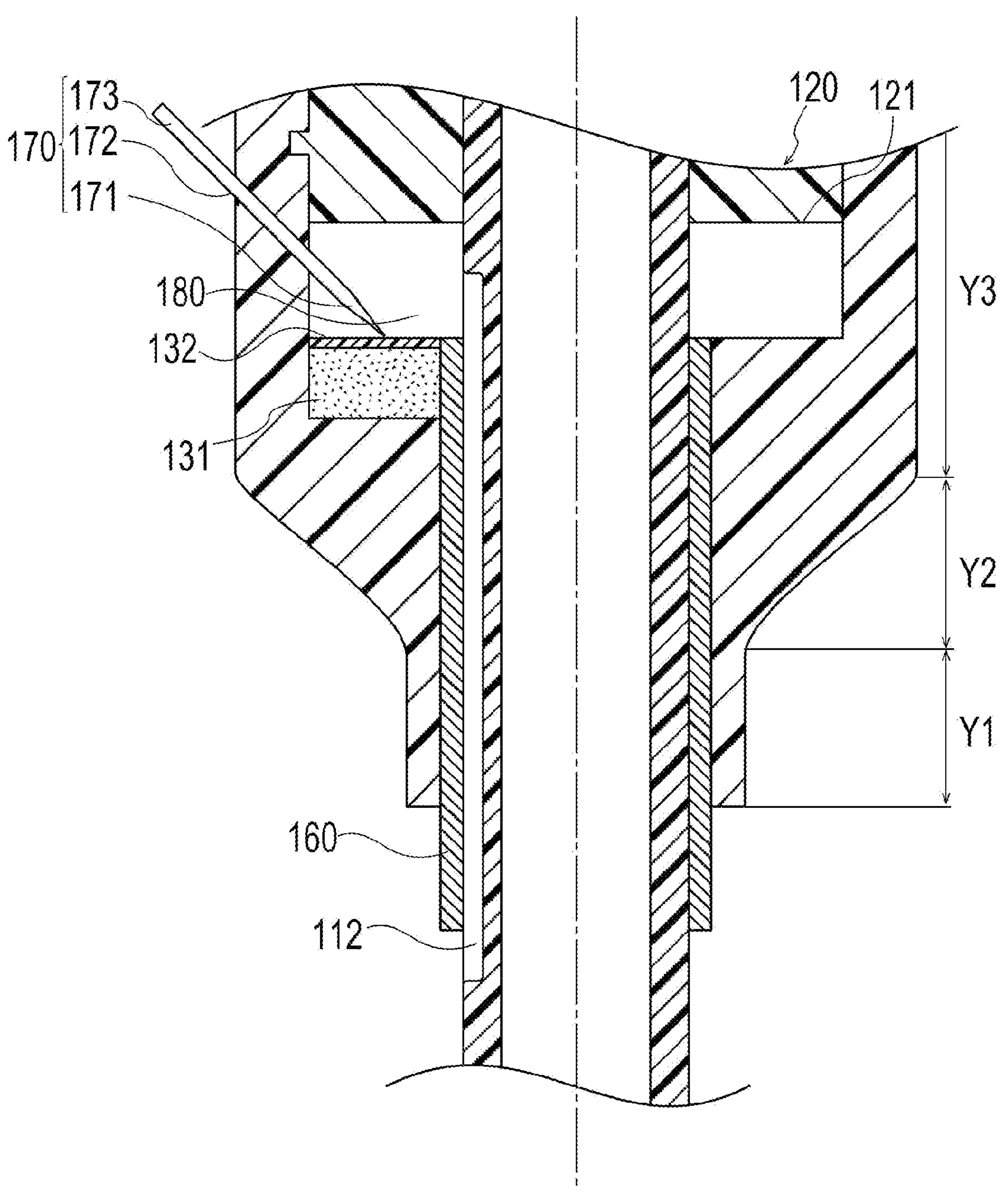
FIG. 3 is an enlarged view of a broken line portion in FIG. 2.

FIGS. 1 to 3 are views for explaining each part of the introducer assembly 10, and FIGS. 4A to 6B are views for explaining a treatment method using the introducer sheath 100.

With reference to FIG. 2, in the present specification, a side of the introducer sheath 100 on which a hub 120 is disposed (upper side in FIG. 2) is referred to as a "proximal side". A side (lower side in FIG. 2) of the introducer sheath 100, which is located opposite to the proximal side and introduced into a biological lumen R, is referred to as a "distal side". Furthermore, a direction in which the introducer sheath 100 extends (vertical direction in FIG. 2) is referred to as an "axial direction or longitudinal direction". Furthermore, a "distal portion" represents a certain range including a distal end (the most distal end) and its periphery, and a "proximal portion" represents a certain range including a proximal end (the most proximal end) and its periphery.

Figure 6A:
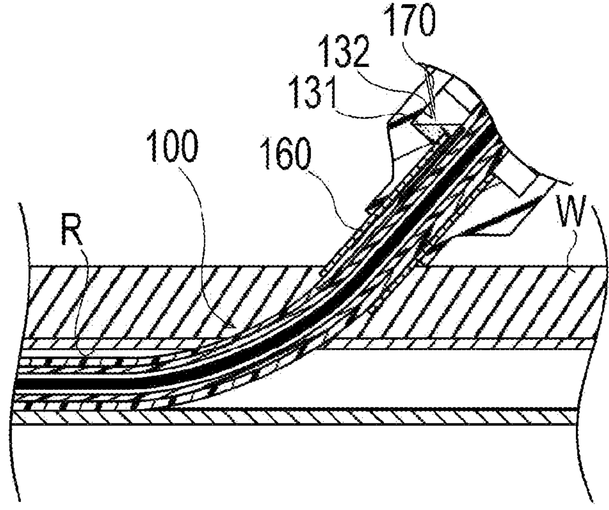
FIG. 6A is a schematic cross-sectional view illustrating a state in which a drug solution of a drug part is introduced into a wound site.
Figure 6B:
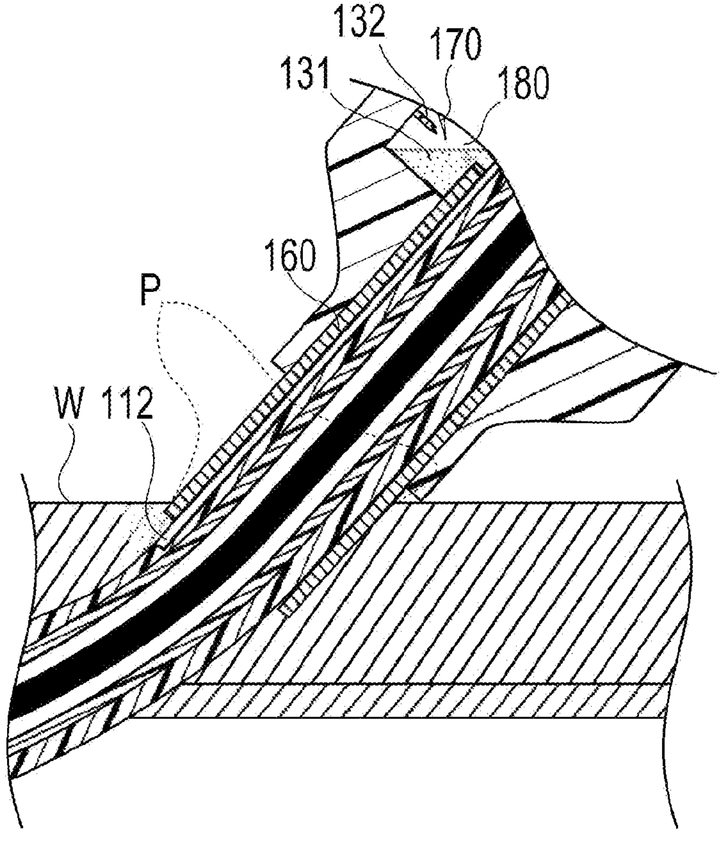
FIG. 6B is an enlarged view illustrating the vicinity of the wound site in FIG. 6A.

Furthermore, with reference to FIGS. 6A and 6B, a site in a biological tissue W such as a puncture site which is wounded or punctured when the introducer sheath 100 is percutaneously introduced into the biological lumen R is referred to as a "wound site P".

As illustrated in FIG. 1, the introducer assembly 10 according to the present embodiment includes an introducer sheath 100 and a dilator 200. Hereinafter, the introducer sheath 100 and the dilator 200 will be described in detail.

Introducer Sheath

The introducer sheath 100 is placed in the biological lumen R such as a blood vessel, and is used for inserting treatment instruments such as a catheter and a guide wire into a lumen 116 of the introducer sheath 100 and introduce the treatment instruments into the biological lumen R. For example, a procedure such as percutaneous transluminal coronary angioplasty (PTCA) also called percutaneous coronary intervention (PCI) can be performed using a guide wire or the like introduced into the biological lumen R. As an approach method of the percutaneous transluminal coronary angioplasty, there are trans femoral intervention (TFI) in which an introducer sheath corresponding to a medical elongated body is introduced from an artery (femoral artery) at the base of a leg and trans radial intervention (TRI) in which an introducer sheath is introduced from an artery (radial artery) of a wrist.

Figure 4A:
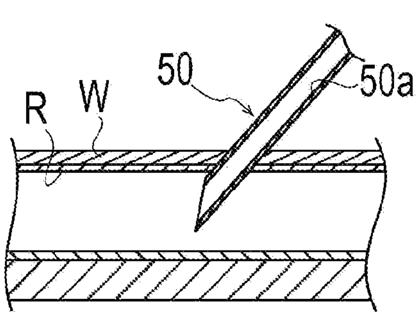
FIGS. 4A to 4F are schematic cross-sectional views explaining a method of placing a medical elongated body according to the first embodiment.
Figure 4B:
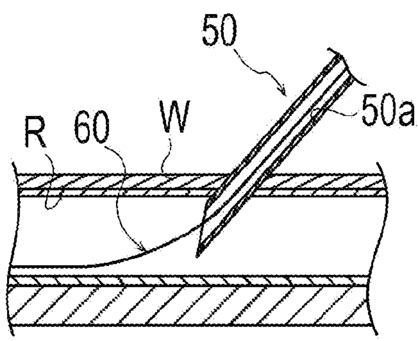
Figure 4C:
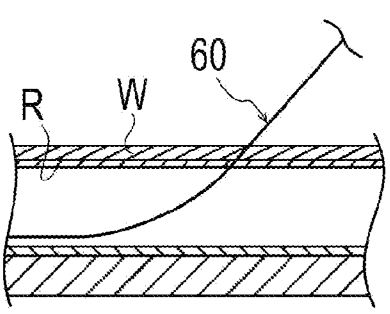
Figure 4C:
Figure 4D:
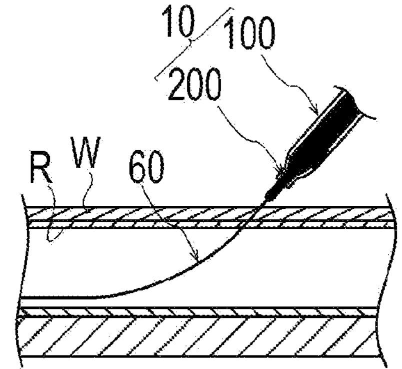
Figure 4E:
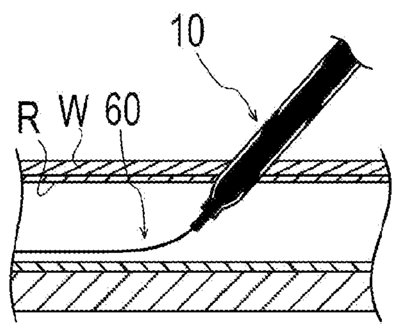
Figure 4F:
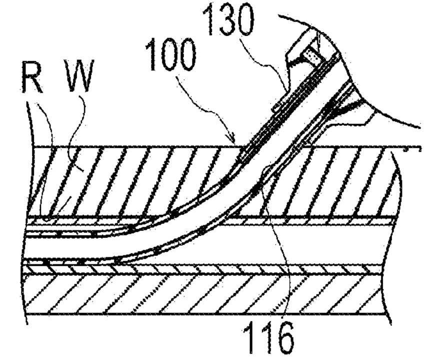

As illustrated in FIGS. 2 and 4F, the introducer sheath 100 includes a catheter body 110 that is percutaneously inserted into the biological lumen R, and a hub 120 connected to a proximal side of the catheter body 110. The introducer sheath 100 includes a support member 130 connected to the hub 120 and configured to cover a part of the proximal side of the catheter body 110, and a cover member 160 that is located (extends) from a position on the proximal side with respect to the distal end of the support member 130 to a position on the distal side with respect to the distal end of the support member 130. The support member 130 includes a drug part 131 and a partition wall portion 132. Details will be described later.

Catheter Body

The catheter body 110 is formed by a substantially cylindrical tubular member in which the lumen 116 extends. As illustrated in FIG. 2, the catheter body 110 includes a tapered distal portion 111, a main body portion 115 located on the proximal side of the distal portion 111, and a proximal portion 113 located on the proximal side of the main body portion 115 and connected to the hub 120.

Furthermore, the catheter body 110 has a groove portion (groove) 112 on the outer surface of the catheter body 110. The groove portion 112 is provided (i.e., extends) from a position on the proximal side of the main body portion 115 of the catheter body 110 to a position on the distal side with respect to the distal end of the support member 130. In addition, at least a part of the groove portion 112 at the position on the proximal side in the longitudinal direction of the catheter body 110 is covered by the support member 130. In the present embodiment, the position of the groove portion 112 on the proximal side in the longitudinal direction of the catheter body 110 is partially covered by the support member 130 and the cover member 160. Therefore, as will be described later, in a state in which the partition wall portion 132 is broken, a drug solution of the drug part 131 can flow out from the proximal side of the groove portion 112 toward the distal side of the groove portion 112.

The groove portion 112 is provided on a part of the outer surface of the catheter body 110 in a circumferential direction of the catheter body 110. In the illustrated embodiment, at least a part of the groove portion 122 is an axially extending part that extends along a portion of the longitudinal extent of the catheter body 110. Furthermore, the shape of the distal portion of the groove portion 112 is not particularly limited as long as it is a shape that allows the drug solution of the drug part 131 to flow out to the wound site P in a state in which the groove portion 112 of the catheter body 110 is inserted into (located in) the wound site P. For example, the distal portion of the groove portion may be configured such that the depth of the groove portion gradually decreases from the proximal side of the groove portion toward the distal side of the groove portion. Furthermore, the groove portion 112 is provided at one position of the catheter body 110 in the circumferential direction.

The depth of the groove portion 112 can be set to range from, for example, equal to or greater than 0.01 mm to equal to or less than 0.15 mm. Furthermore, the length of the groove portion 112 (length in the longitudinal direction of the catheter body 110) can be set to range from, for example, equal to or greater than 10 mm to equal to or less than 30 mm.

The groove portion 112 is configured to face a space portion (space) 180 of the support member 130 to be described later. That is, a space formed by the groove portion 112 is connected to the space portion 180 of the support member 130. Therefore, when the operator breaks the partition wall portion 132, the drug solution of the drug part 131 flows to the groove portion 112 through the space portion 180 and flows out to the wound site P from the distal side of the groove portion 112. Therefore, the operator can administer the drug solution to the wound site P.

A constituent material from which the catheter body 110 may be fabricated is not particularly limited, and for example, a polymer material such as polyolefin (for example, polyethylene, polypropylene, polybutene, an ethylene-propylene copolymer, an ethylene-vinyl acetate copolymer, an ionomer, a mixture of two or more thereof, or the like), polyolefin elastomer, crosslinked polyolefin, polyvinyl chloride, polyamide, polyamide elastomer, polyester, polyester elastomer, polyurethane, polyurethane elastomer, a fluororesin, polycarbonate, polystyrene, polyacetal, polyimide, polyetherimide, polyetheretherketone, or a mixture thereof can be used.

Hub

The hub 120 is fixed to the proximal portion of the catheter body 110. As illustrated in FIG. 2, the hub 120 includes a lumen 122 to which the proximal portion 113 of the catheter body 110 is fixed, and a side port 124 communicating with the lumen 122.

One end of a flexible tube 151 (see FIG. 1) is liquid-tightly connected to the side port 124. For example, a three-way stopcock 150 is attached to the other end of the tube 151. A liquid such as physiological saline can be injected into the lumen 116 of the catheter body 110 from a port of the three-way stopcock 150 through the tube 151. The tube 151 can be, for example, a known tube made of polyvinyl chloride.

A constituent material from which the hub 120 may be fabricated is not particularly limited, but a hard material such as a hard resin is suitable. Specific examples of the hard resin include polyolefin such as polyethylene or polypropylene, polyamide, polycarbonate, and polystyrene.

A hemostatic valve 140 for preventing blood flowing into the catheter body 110 from leaking to the outside is attached to a proximal portion 123 of the hub 120. The hemostatic valve 140 include an elastic member having a cross cut 140*a* that allows a dilator body 210 to be inserted. The hemostatic valve 140 has a substantially elliptical membrane shape (disk shape) and is fixed in liquid-tight manner to the hub 120 as a result of fitting of a predetermined cap 145.

A constituent material from which the hemostatic valve 140 may be fabricated is not particularly limited, and examples thereof include silicone rubber, latex rubber, butyl rubber, or isoprene rubber as the elastic member The proximal portion 113 of the catheter body 110 is fixed to an interlock portion 125*a* of the hub 120. The proximal portion 113 of the catheter body 110 and the interlock portion 125*a* of the hub 120 can be fixed by, for example, an adhesive.

Support Member

The support member 130 is connected to the hub 120 and is configured to cover a part of the proximal side (proximal end portion) of the catheter body 110. As illustrated in FIG. 2, the support member 130 is externally fitted to the catheter body 110 and the hub 120. The support member 130 covers a distal portion 121 of the hub 120 and surrounds a predetermined range or predetermined axial extent of the proximal side of the catheter body 110. The support member may be fixed to the hub with an adhesive or the like, or may be detachably connected to the hub by fitting to each other.

The support member 130 covers the catheter body 110 and the hub 120 to prevent the catheter body 110 from kinking between the catheter body 110 and the hub 120 when the operation of inserting the introducer sheath 100 into the biological lumen is performed.

The constituent material from which the support member 130 (other than the partition wall portion 132) may be fabricated is not particularly limited, and examples thereof include natural rubber and a silicone resin. Furthermore, as a constituent material from which the partition wall portion 132 of the support member 130 may be fabricated, natural rubber, silicone resin, or the like may be used as in the case of the constituent material of the support member 130 (other than the partition wall portion 132), or a resin material such as polyvinylidene chloride or polyvinyl chloride may be used. The partition wall portion 132 of the support member 130 is preferably made of the same material as the constituent material of the support member 130 (other than the partition wall portion 132) from the viewpoint of fusibility to the support member 130 (other than the partition wall portion 132) or ease of installation to the support member 130 (other than the partition wall portion 132).

As illustrated in FIG. 2, the support member 130 includes the drug part 131 having a drug solution, and the partition wall portion 132 located between the drug part 131 and the groove portion 112.

The drug part 131 has or includes, for example, a solution containing a known material having an effect on hemostasis, such as a metal ion that promotes the repair of the wound site P, and a hemostatic agent such as transamine or sodium carbazochrome sulfonate.

With reference to FIGS. 2 and 3, the drug part 131 is disposed in the internal space of the support member 130. FIGS. 2 and 3 show that the drug part 131 is an enclosed part enclosing or containing the drug solution. The drug part 131 is held in the internal space of the support member 130 by the partition wall portion 132.

Since the drug part 131 is held in the internal space of the support member 130, the drug part 131 does not come into contact with the biological tissue W when the introducer sheath 100 is percutaneously inserted into or positioned in the biological lumen R. Therefore, the drug part 131 is not lost by abrasion (i.e., is not removed by contact) when the introducer sheath 100 is inserted into the biological lumen R, or the drug solution of the drug part 131 is not administered to the biological tissue W at a timing not intended by the operator. Furthermore, the drug part 131 releases a part of the drug solution when the partition wall portion 132 is broken by a needle member (needle) 170, and causes the drug solution to flow to the biological tissue W via the groove portion 112. Therefore, the drug solution can be brought into contact with the biological tissue W. Therefore, after a diagnosis device or a treatment device is introduced through the introducer sheath 100 and diagnosis or treatment for the lesion site of the biological lumen R is performed, before the introducer sheath 100 is withdrawn from the biological lumen R, the operator can administer the drug solution to the wound site P at any timing and shorten the hemostasis time at the wound site P by the hemostatic action of the drug solution.

With reference to FIG. 3, the partition wall portion 132 of the support member 130 is configured to make the drug part 131 communicate with the groove portion 112 when the partition wall portion 132 is broken by causing damage to the partition wall portion 132. Specifically, the partition wall portion 132 forms a part of the inner surface of the support member 130 that covers the outer surface of the catheter body 110, and prevents the drug solution of the drug part 131 from being released to the outside of the support member 130.

Accordingly, the support member 130 can release the drug solution of the drug part 131 and allow the drug solution to flow out to the groove portion 112 of the catheter body 110 when the partition wall portion 132 is broken. Therefore, the operator can release the drug solution of the drug part 131 accommodated in the internal space of the support member 130 into the groove portion 112 by breaking the partition wall portion 132, and can administer the drug solution of the drug part 131 to the wound site P in a state in which the introducer sheath 100 is placed in the biological lumen R.

The space portion 180 is formed between the catheter body 110 and the support member 130 in a state in which the support member 130 is attached to the catheter body 110 (in a state in which the support member 130 is externally fitted to the catheter body 110 and the hub 120). Specifically, the space portion 180 is formed between the outer surface of the catheter body 110 and the inner surface of the support member 130 at a position connected to the space formed by the groove portion 112 of the catheter body 110. The space portion 180 is adjacent to the drug part 131 with the partition wall portion 132 interposed between the catheter body 110 and the support member 130. In the present embodiment, as illustrated in FIG. 3, the space portion 180 is located on the proximal side with respect to the drug part 131 and the partition wall portion 132.

Furthermore, the partition wall portion 132 is broken by the needle member 170. The needle member 170 has a sharp distal portion 171 capable of breaking the partition wall portion 132, a main body portion 172 located on the proximal side with respect to the distal portion 171, and a base portion 173 located outside the support member 130. In the present embodiment, as illustrated in FIG. 3, the distal portion 171 of the needle member 170 is in a state of being inserted into or positioned in the support member 130 so as to be directed toward the distal side of the catheter body 110. Furthermore, the distal portion 171 of the needle member 170 is located in the space portion 180, and a part of the main body portion 172 is located outside the support member 130. The base portion 173 is located at a position different from the drug part 131 in the longitudinal direction of the catheter body 110.

In the present embodiment, as illustrated in FIG. 2, the shape of the support member 130 includes a distal region Y1, an intermediate region Y2 connected to the distal region Y1, disposed on the proximal side of the catheter body 110 with respect to the distal region Y1, and extending to be inclined in a direction away from the outer surface of the catheter body 110, and a proximal region Y3 connected to the intermediate region Y2 and disposed on the proximal side with respect to the intermediate region Y2. In the present embodiment, as illustrated in FIG. 2, in order to secure the space of the drug part 131 and the space of the space portion 180, the drug part 131 and the partition wall portion 132 are disposed in the proximal region Y3 of the support member 130. The proximal region Y3 of the support member 130 is a region connected to the hub 120, and has an outer diameter greater than the outer diameters of the distal region Y1 and the intermediate region Y2.

However, the shape of the support member 130 is not limited to this as long as the drug part 131, the partition wall portion 132, and the space portion 180, which are described above, can be formed. Furthermore, in the present embodiment, the drug part 131 is provided not on the entire circumference but on a part of the circumference of the support member 130 in the circumferential direction (angular direction) so that the drug part has a limited circumferential extent, but may be provided on the entire circumference in the internal space of the support member.

Cover Member

The cover member 160 is located or extends from a position on the proximal side with respect to the distal end of the support member 130 to a position on the distal side with respect to the distal end of the support member 130 in the longitudinal direction of the catheter body 110. In the present embodiment, as illustrated in FIG. 3, the cover member 160 is fixed to the support member 130 and configured to cover a part of the groove portion 112. In the illustrated embodiment, the cover member 160 axially overlaps and covers an axially extending part of the groove portion 112. Furthermore, in the present embodiment, the cover member 160 is fixed to the support member 130 in a state in which a predetermined interval is provided between the proximal end of the cover member 160 and the hub 120. That is, the proximal end of the cover member 160 is spaced distally from the support member 130. Therefore, the proximal end of the groove portion 112 is positioned between the proximal end of the cover member 160 and the hub 120 in the longitudinal direction of the catheter body 110 so as to face the space portion 180. Furthermore, the distal end of the cover member 160 is located on the proximal side of the distal end of the groove portion 112.

During use, the cover member 160 is disposed in the biological tissue W such that the distal end of the groove portion 112 of the catheter body 110 is located at the wound site P in a state in which the catheter body 110 is inserted into or positioned in the biological tissue W. Therefore, it is preferable that the cover member 160 is configured such that the outer diameter of the cover member 160 is greater than the outer diameter of the catheter body 110 so as to obtain the effect of preventing the catheter body 110 from coming off from or being removed from the biological tissue W. Furthermore, it is preferable that the cover member 160 is made of a metal material or a fluorine resin harder than the material of the catheter body 110 such that the outer diameter of the cover member 160 can be maintained and the cover member 160 can be smoothly inserted into the biological tissue W when the catheter body 110 is inserted into the biological tissue W. In the cover member 160, in order to obtain the effect of preventing the catheter body 110 from coming off, the surface of the cover member 160 may be partially or entirely subjected to a treatment for increasing the surface roughness (blasting or the like).

Dilator

As illustrated in FIG. 1, the dilator 200 includes a dilator body 210 formed by a tubular body that can be inserted into or positioned in the catheter body 110, and a dilator hub 220 connectable to the hub 120.

The dilator 200 is used to prevent breakage of the catheter body 110 or to expand dermal perforations when the catheter body 110 of the introducer sheath 100 is inserted into the biological lumen R.

When the dilator body 210 is inserted into the catheter body 110, a distal portion 211 of the dilator body 210 protrudes from the distal portion 111 of the catheter body 110. The distal portion 211 of the dilator body 210 is formed in a tapered shape tapered toward the distal side.

The material constituting the dilator body 210 is not particularly limited, and the same material as that used in the related art can be used as the dilator body 210. Specific examples of the material of the dilator body 210 include polyolefin such as polypropylene (PP) and polyethylene (PE), polyester such as nylon and polyethylene terephthalate (PET), and fluoropolymer such as polyvinylidene fluoride (PVDF) and tetrafluoroethylene-hexafluoropropylene copolymer (FEP).

The constituent material from which the dilator hub 220 may be fabricated is not particularly limited, but a hard material such as a hard resin is suitable. Specific examples of the hard resin include polyolefin such as polyethylene or polypropylene, polyamide, polycarbonate, and polystyrene.

Next, a usage example of the introducer sheath 100 will be described with reference to FIGS. 4A to 4F, 5, and 6A to 6B.

In FIGS. 4A to 4F, the introducer sheath 100 is percutaneously inserted into the biological lumen R through the wound site P such as the puncture site formed on the limb of the patient, and the catheter body 110 of the introducer sheath 100 is placed in the biological lumen R. Specifically, in FIGS. 4A to 4F, the biological lumen R in which the introducer sheath 100 is to be placed is punctured with an introduction needle 50 (see FIG. 4A); a guide wire 60 is inserted into the biological lumen R through a lumen 50*a* of the introduction needle 50 (see FIG. 4B); the introduction needle 50 is withdrawn from the biological lumen R after the guide wire 60 is placed or located in the biological lumen R, and the guide wire 60 remains in the biological lumen R (see FIG. 4C); puncturing with the introducer assembly 10 is performed with the dilator 200 directed along the guide wire 60 placed in the biological lumen R (see FIGS. 4D and 4E); and the guide wire 60 and the dilator 200 are withdrawn from the introducer sheath 100 while the introducer sheath 100 remains in the biological lumen R (see FIG. 4F). When the catheter body 110 is placed in the biological lumen R, the introducer sheath 100 is disposed such that the distal end of the groove portion 112 of the catheter body 110 is located in the biological tissue through the wound site P.

After placing the introducer sheath 100 in the biological lumen R, the operator introduces the treatment instrument such as the catheter or the guide wire into the biological lumen R through the hemostatic valve 140 of the introducer sheath 100, and performs treatment (for example, a procedure such as percutaneous transluminal coronary angioplasty) for a lesion site in the biological lumen R.

Figure 5:
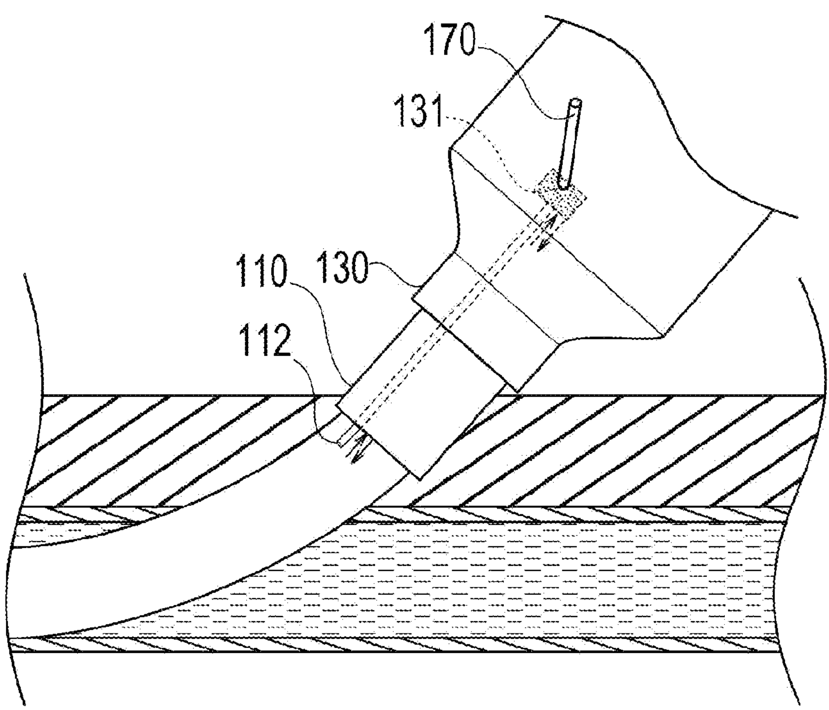
FIG. 5 is a view illustrating a state in which a medical elongated body is placed in a biological lumen.

After a predetermined procedure is completed, as illustrated in FIGS. 5 and 6A, the operator presses the base portion 173 of the needle member 170 located outside the support member 130 in a state in which the distal end of the groove portion 112 of the catheter body 110 is located in the biological tissue, causes the distal portion 171 of the needle member 170 to approach the partition wall portion 132 from the space portion 180, and breaks the partition wall portion 132 by causing damage. Accordingly, the drug solution of the drug part 131 is released toward the distal side of the groove portion 112 via the space portion 180 and the groove portion 112. Then, the drug solution of the drug part 131 is administered to the wound site P through the distal end of the groove portion 112. In the introducer sheath 100, the groove portion 112 and the space portion 180 may be filled with blood or the like during the predetermined procedure. In this case, when the base portion 173 of the needle member 170 located outside the support member 130 is pressed to break the partition wall portion 132, the drug solution of the drug part 131 is released into blood or the like and administered to the wound site P through the distal end of the groove portion 112. Furthermore, a timing at which the operator presses the base portion 173 of the needle member 170 and breaks the partition wall portion 132 may be a timing before the predetermined procedure is completed. For example, the operator may press the base portion 173 of the needle member 170 to break the partition wall portion 132 and administer the medicinal solution into the biological tissue during the predetermined procedure in consideration of the penetration time of the drug solution of the drug part 131 into the biological tissue.

Thereafter, as illustrated in FIG. 6B, the drug solution of the drug part 131, which is administered to the wound site P, is absorbed by the wound site P and the biological tissue around the wound site P, and the wound is treated to stop bleeding. After the predetermined procedure is completed and the drug solution of the drug part 131 is administered to the wound site P, the introducer sheath 100 is withdrawn from the biological lumen R. At this time, in order to shorten the hemostasis time with the drug solution, compression hemostasis may be performed with a hemostatic instrument or the like as necessary when the introducer sheath 100 is withdrawn from the biological lumen.

As described above, the introducer sheath 100 according to the present embodiment includes the catheter body 110, the hub 120 fixed to the proximal portion of the catheter body 110, and the support member 130 connected to the hub 120 and configured to cover a part of the proximal side of the catheter body 110. The catheter body 110 has the groove portion 112 on the outer surface of the catheter body 110. The support member 130 is disposed so as to partially cover the groove portion 112. The support member 130 includes the drug part 131 having the drug solution, and the partition wall portion 132 located between the drug part 131 and the groove portion 112. The partition wall portion 132 is configured to make the drug part 131 communicate with the groove portion 112 in a state of being broken by causing damage.

With this configuration, it is possible to administer the drug solution to the wound site P via the groove portion 112 of the catheter body 110 by a simple operation, and it is possible to shorten the time required for hemostasis at the wound site P of the patient and lessen the burden on the patient and the operator. That is, in the introducer sheath 100, the catheter body 110 is percutaneously inserted into the blood vessel from the wound site P, and the partition wall portion 132 of the support member 130 is broken by a simple operation such as compression of the support member 130 in a state in which the groove portion 112 of the catheter body 110 is inserted into the wound site P. Therefore, the drug solution of the drug part 131 of the support member 130 can be administered to the wound site P via the groove portion 112 of the catheter body 110. Furthermore, since the operation of the operator administering the drug solution to the wound site P by using the introducer sheath 100 is only the operation of breaking the partition wall portion 132, the drug solution can be administered to the wound site P without moving the catheter body 110 placed in the wound site P. In addition, since the introducer sheath 100 is disposed such that the support member 130 partially covers the groove portion 112, it is possible to prevent the operator from touching the drug solution when the operator administers the drug solution to the wound site P. Therefore, the operator can administer the drug solution to the wound site P with a simple operation, and the hemostasis time at the wound site P can be shortened by the hemostatic action of the drug solution. In particular, in a case of being used in combination with the hemostatic instrument for stopping bleeding by compressing the wound site P such as the puncture site, the hemostasis time can be shortened by the drug solution. Therefore, it is possible to reduce the labor and time for the operator's decompression operation and reduce the risk of artery occlusion and the like. Moreover, since the introducer sheath 100 includes the partition wall portion 132 between the drug part 131 and the groove portion 112, after the catheter body 110 is percutaneously inserted into the blood vessel from the wound site P, it is possible to prevent the drug solution from being administered to the wound site P in a state before the partition wall portion 132 is broken. Therefore, the operator can break the partition wall portion 132 of the support member 130 by giving pressure or causing damage and administer the drug solution to the wound site P at any timing.

Furthermore, the introducer sheath 100 includes the needle member 170 having the distal portion 171 configured to break the partition wall portion 132, and the space portion 180 adjacent to the drug part 131 with the partition wall portion 132 interposed therebetween between the catheter body 110 and the support member 130. The distal portion 171 of the needle member 170 is located in the space portion 180. In this manner, the distal portion 171 of the needle member 170 is located in the space portion 180 adjacent to the drug part 131 with the partition wall portion 132 interposed therebetween. Therefore, by moving the distal portion 171 of the needle member 170 from the space portion 180 to the partition wall portion 132, the operator can easily break the partition wall portion 132 and release the drug solution of the drug part 131. Therefore, the operator can administer the drug solution of the drug part 131 of the support member 130 to the wound site P via the groove portion 112 of the catheter body 110 in a state in which the groove portion 112 of the catheter body 110 is inserted into or positioned in the wound site P.

Furthermore, the needle member 170 has the distal portion 171 and the main body portion 172 located on the proximal side with respect to the distal portion 171, and a part of the main body portion 172 of the needle member 170 is located outside the support member 130. As described above, in the needle member 170, a part of the main body portion 172 of the needle member 170 is located outside the support member 130. Therefore, the operator can manipulate the distal portion 171 of the needle member 170 and break the partition wall portion 132 by manipulating a part of the main body portion 172 of the needle member 170 located outside the support member 130. Therefore, in a state in which the groove portion 112 of the catheter body 110 is inserted into or positioned in the wound site P, the operator can manipulate the needle member 170 located outside the support member 130, and can more easily administer the drug solution of the drug part 131 of the support member 130 to the wound site P via the groove portion 112 of the catheter body 110.

Furthermore, the needle member 170 has the base portion 173 located outside the support member 130, and the base portion 173 is located at a position different from the drug part 131 in the longitudinal direction of the catheter body 110. Accordingly, the needle member 170 is obliquely disposed such that the distal portion 171 of the needle member 170 is located to face the drug part 131 and the base portion 173 of the needle member 170 is located at a position different from the drug part 131 in the longitudinal direction of the catheter body 110. Accordingly, the needle member 170 can prevent the distal portion 171 of the needle member 170 from moving in a direction perpendicular to the longitudinal direction of the catheter body 110 when the operator manipulates the needle member 170. Therefore, even when the distal portion 171 of the needle member 170 is inserted deeper than expected, the distal portion 171 of the needle member 170 can be made difficult to reach the catheter body 110 and the cover member 160, and it is possible to prevent the distal portion 171 of the needle member 170 from damaging the catheter body 110 and the cover member 160. Note that, the hub 120 is made of a material harder than that of the catheter body 110. Therefore, it is preferable that the distal portion 171 of the needle member 170 faces the hub 120. With this configuration, it is possible to more reliably prevent the distal portion 171 of the needle member 170 from damaging the catheter body 110 when the operator manipulates the needle member 170. Therefore, it is more preferable that the base portion 173 of the needle member 170 is located at a position different from the drug part 131 in the longitudinal direction of the catheter body 110, and the distal portion 171 of the needle member 170 faces the hub 120.

Furthermore, the introducer sheath 100 includes the cover member 160 that is located (extends) from a position on the proximal side with respect to the distal end of the support member 130 to a position on the distal side with respect to the distal end of the support member 130 in the longitudinal direction of the catheter body 110. The cover member 160 covers at least a part of the groove portion 112, and the distal end of the cover member 160 is disposed so as to be located on the proximal side with respect to the distal end of the groove portion 112. In this manner, the cover member 160 covers the groove portion 112 from a position on the proximal side with respect to the distal end of the support member 130. Therefore, the cover member 160 can prevent the drug solution from coming into contact with the operator's hand when the operator releases the drug solution. Furthermore, the cover member 160 is located on the proximal side with respect to the distal end of the groove portion 112. Therefore, since the operator can visually recognize the position of the distal end of the groove portion 112 from which the drug solution is released, when the introducer sheath 100 is placed in the biological lumen, the distal end of the groove portion 112 from which the drug solution is released can be easily disposed so as to be located in the biological tissue. Furthermore, since the cover member 160 is located or extends from a position on the proximal side with respect to the distal end of the support member 130 to a position on the distal side with respect to the distal end of the support member 130 and covers the groove portion 112 in which the thickness of the catheter body 110 is thin, the rigidity of the introducer sheath 100 is improved. Therefore, the cover member 160 prevents the catheter body 110 from kinking at the distal end of the support member 130 when the operator places the introducer sheath 100 in the biological lumen. Furthermore, the scale may be provided to the cover member 160. Accordingly, the operator can recognize the distal position of the groove portion 112 even in a state in which the introducer sheath 100 is placed in the biological lumen, and thus, can easily recognize the distal position of the groove portion 112 even in a case where the catheter body 110 is moved during a predetermined procedure.

First Modification Example of First Embodiment

Figures 7A, 7B:
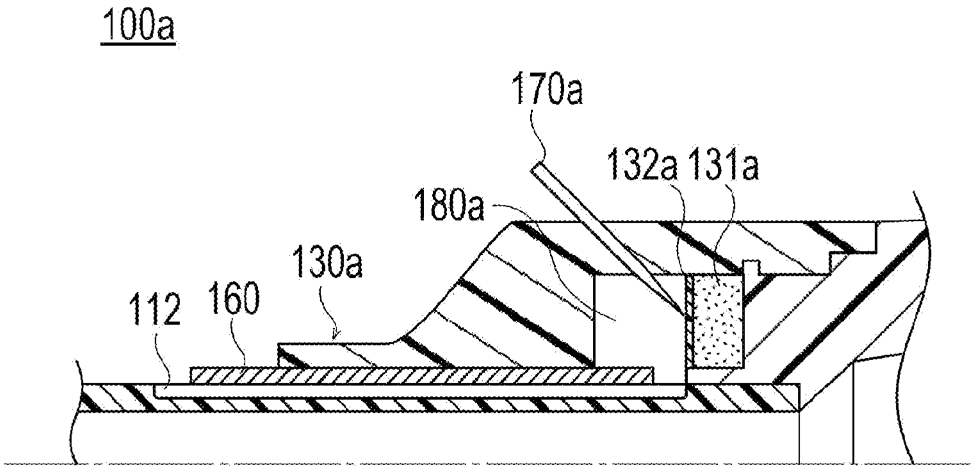
FIGS. 7A and 7B are views illustrating modification examples of a support member and needle member and illustrating a portion corresponding to the left side of the center line of FIG. 3.

FIG. 7A is a view illustrating an introducer sheath 100*a* according to the first modification example of the first embodiment and corresponding to the left side of the center line of FIG. 3. In the first embodiment, it has been described that the space portion 180 is located on the proximal side of the catheter body 110 with respect to the drug part 131 and the partition wall portion 132, and the distal portion 171 of the needle member 170 is positioned in the support member 130 and directed toward the distal side of the catheter body 110. However, the distal portion of the needle member may be directed toward the proximal side of the catheter body as in the present modification example. In the present modification example, the configurations of a drug part 131*a*, a partition wall portion 132*a*, a space portion 180*a*, and a needle member 170*a*, which are included in a support member 130*a*, are different from those of the first embodiment, and the configurations of the other features are the same as those of the first embodiment. Therefore, a detailed description of the configuration common to the first embodiment will not be repeated.

As shown in FIG. 7A, the space portion 180*a* is located on the distal side of the catheter body 110 with respect to the drug part 131*a* and the partition wall portion 132*a*. That is, the space portion 180*a* is distal of the drug part 131*a* and the partition wall portion 132*a*. The configurations of the other parts of the drug part 131*a* and the partition wall portion 132*a* are the same as those of the first embodiment, and thus the description thereof is not repeated.

The needle member 170*a* has the distal portion 171, the main body portion 172, and the base portion 173 similar to the needle member 170 of the first embodiment. The needle member 170*a* differs from the needle member 170 of the first embodiment in that the distal portion 171 of the needle member 170 is inserted into or positioned in the support member 130*a* so as to be directed toward the proximal side of the catheter body 110. The configurations of other aspects of the needle member 170*a* are the same as the configurations of the first embodiment, and thus the description thereof is not repeated.

Furthermore, a treatment method using the introducer sheath 100*a* according to the present modification example is similar to that of the first embodiment, and thus the description thereof is not repeated.

In the first modification example described above, the space portion 180*a* is located on the distal side of the catheter body 110 with respect to the drug part 131*a* and the partition wall portion 132*a*, and the needle member 170*a* is inserted into or positioned in the support member 130*a* such that the distal portion 171 of the needle member 170*a* is directed toward the proximal side of the catheter body 110. With this configuration, it is possible to administer the drug solution to the wound site P via the groove portion 112 of the catheter body 110 with a simple operation as in the first embodiment, and it is possible to shorten the time required for hemostasis at the wound site P of the patient and lessen the burden on the patient and the operator.

Second Modification Example of First Embodiment

FIG. 7B is a view illustrating an introducer sheath 100*b* according to the second modification example of the first embodiment and corresponding to the left side of the center line of FIG. 3. It has been described that the needle member 170 of the first embodiment and the needle member 170*a* of the first modification example are in a state of being inserted into or positioned in the support member 130 or the support member 130*a* in a state in which the main body portion 172 and base portion 173 of the needle members 170 and 170*a* are exposed to the outside of the support member 130 or the support member 130*a*. However, the support member may include a convex portion (cover) covering at least the main body portion of the needle member. The second modification example is different from the first modification example in that in the introducer sheath 100*a*, a support member 130*b* includes a convex portion or cover 134, and the configurations of other aspects are the same as those of the first modification example. Therefore, a detailed description of the features common to the second modification example and the first modification example is not repeated.

The convex portion 134 covers the main body portion 172 and base portion 173 of the needle member 170*a* located outside the support member 130*b*. The convex portion 134 is provided on the outer surface of the support member 130*b* while covering the main body portion 172 and base portion 173 of the needle member 170*a*. The convex portion 134 is configured to press the main body portion 172 and base portion 173 of the needle member 170*a* and move the distal portion of the needle member 170*a* toward the partition wall portion 132*a* when the operator presses the convex portion 134. A constituent material from which the convex portion 134 may be fabricated is not particularly limited. For example, the convex portion 134 may be made of a resin material such as a polyamide resin or a polycarbonate resin, or a metal material, or may be made of the same constituent material as that of the support member 130*b*, such as silicone rubber. It is preferable that the convex portion 134 is made of a material having hardness higher than the constituent material of the support member 130*b* such that the operator can press the convex portion 134 and easily press the needle member 170*a*.

A treatment method using an introducer sheath 100*b* according to the second modification example is different from that of the first embodiment in the operation of breaking the partition wall portion 132*a* when the drug solution of the drug part 131*a* is administered to the wound site P. In the first embodiment, the operator performs an operation of pressing the base portion 173 of the needle member 170 located outside the support member 130 in a state in which the groove portion 112 of the catheter body 110 is inserted into or positioned in the wound site P. On the other hand, in the second modification example, the operator performs an operation of pressing the convex portion 134 with a finger in a state in which the groove portion 112 of the catheter body 110 is inserted into or positioned in the wound site P. Accordingly, the pressure of the finger is transmitted to the entire surface of the convex portion 134, the convex portion 134 moves radially inward of the support member 130*b*, and the main body portion 172 covered by the convex portion 134 is pressed and moved toward the distal side of the needle member 170*a*, and the distal portion 171 of the needle member 170*a* breaks the partition wall portion 132*a* by causing damage. Other aspects are the same as the first modification example of the first embodiment, and so a detailed description thereof is not repeated.

As described above, in the introducer sheath 100*b* according to the second modification example, the support member 130*b* includes the convex portion 134 covering the main body portion 172 of the needle member 170*a* located outside the support member 130*b*. Therefore, the operator can easily recognize the proximal position of the needle member 170*a* with the position of the convex portion 134, and can press the distal portion of the needle member 170*a* toward the partition wall portion 132*a* by the pressing operation for the convex portion 134.

Third Modification Example of First Embodiment

Figure 8:
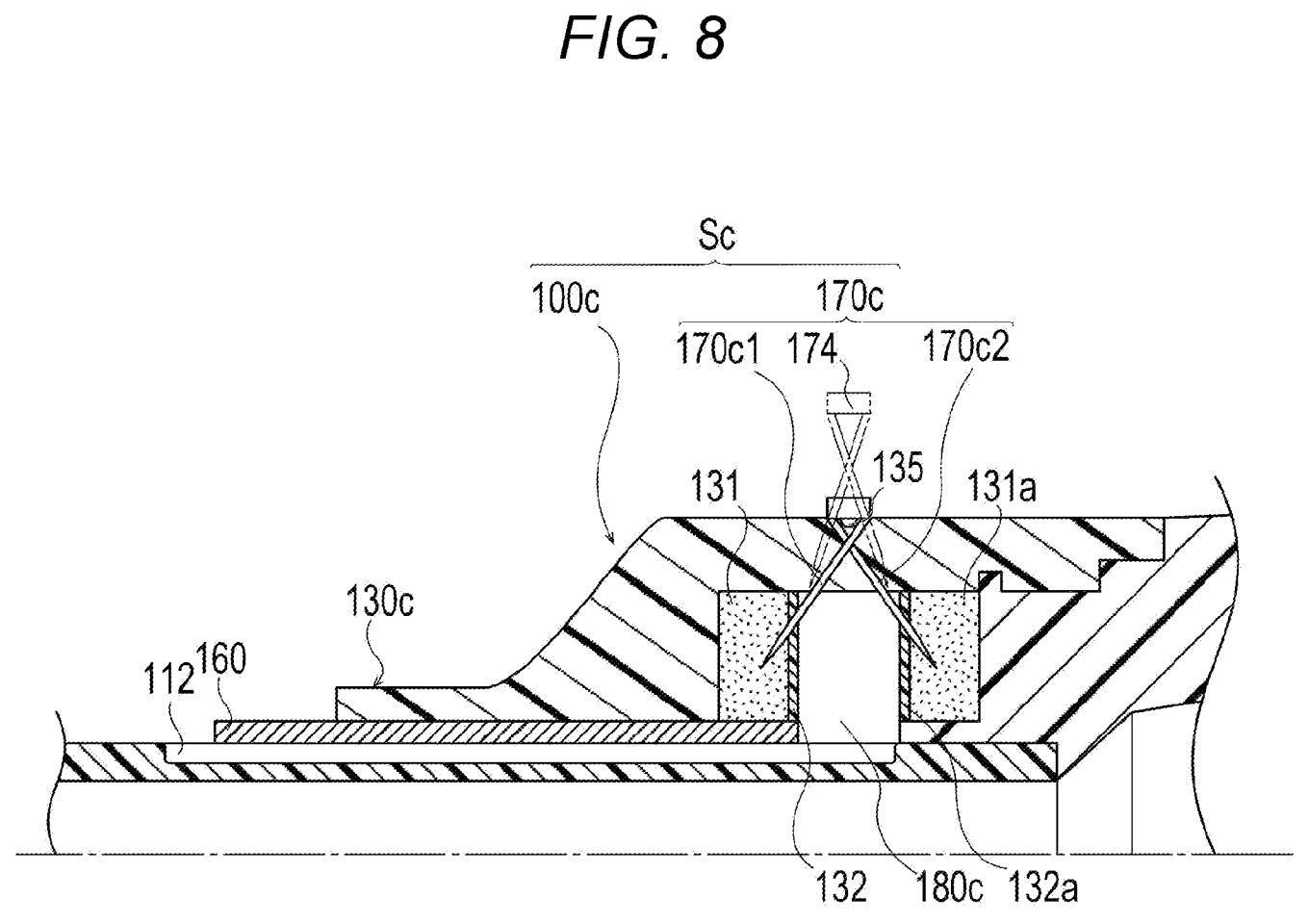

FIG. 8 is a view illustrating a medical elongated body set Sc according to the third modification example of the first embodiment and corresponds to the left side of the center line of FIG. 3. In the first embodiment, the first modification example, and the second modification example, it has been described that the needle members 170 and 170*a* are in the state of being inserted into or positioned in the support members 130, 130*a*, and 130*b*, but the medical elongated body is not limited in this regard. In the medical elongated body, a needle member 170*c* may not be inserted into or positioned in the support member 130*c* before use, and the operator may insert the needle member 170*c* into a support member 130*c* at the time of use.

The medical elongated body set Sc of the third modification example includes an introducer sheath 100*c* and the needle member 170*c*. In the medical elongated body set Sc, the introducer sheath 100*c* and the needle member 170*c* are separated from each other in an unused state. That is, the introducer sheath 100*c* is in a state in which the needle member 170 is not inserted into or positioned in the support member 130 in the introducer sheath 100. Furthermore, the introducer sheath 100*c* according to the present modification example differs from that of the first embodiment in the configurations of the drug part, the partition wall portion, the space portion, and the needle member, which are included in the support member 130*c*. The configurations of the other aspects are the same. Therefore, a detailed description of the configurations of the other features common to the third modification example and the first embodiment is not repeated.

In the third modification example, the needle member 170*c* is not inserted into or positioned in the support member 130*c* in advance. The needle member 170*c* is configured as a separate member from the introducer sheath 100*c*. The support member 130*c* includes a marker portion 135 serving as a mark when the needle member 170*c* is inserted in the circumferential direction of the catheter body 110. In the third modification example, as illustrated in FIG. 8, when the operator presses the base portion 173 of the needle member 170*c* in a direction orthogonal to the longitudinal direction of the catheter body 110, the distal portion of the needle member 170*c* moves obliquely with respect to a direction orthogonal to the longitudinal direction of the catheter body 110. Therefore, the marker portion 135 is provided at a position different from the drug parts 131 and 131*a* in the longitudinal direction of the catheter body 110. In the present embodiment, the marker portion 135 is formed by providing a recess on the outer surface of the support member 130*c*. However, the specific configuration of the marker portion is not limited to the recess as long as a user such as the operator can visually recognize the insertion position of the needle member 170*c*.

As illustrated in FIG. 8, the support member 130*c* includes the drug parts 131 and 131*a* and the partition wall portions 132 and 132*a*. The drug part 131 and the partition wall portion 132 are located on the distal side of the catheter body 110 with respect to a space portion 180*c*. The drug part 131*a* and the partition wall portion 132*a* are located on the proximal side of the catheter body 110 with respect to the space portion 180*c*. In the present modification example, as illustrated in FIG. 8, the drug part and the partition wall portion are provided at two positions on the support member. In a case where the drug part and the partition wall portion are provided only at one position in the support member, it is preferable to provide the drug portion and the partition wall portion on the proximal side of the catheter body since the drug solution of the drug part 131 easily flows out to the distal side of the groove portion 112 by gravity in a state in which the groove portion 112 of the catheter body 110 is inserted into the wound site P.

As illustrated in FIG. 8, the needle member 170*c* has a first needle member 170*c*1, a second needle member 170*c*2, and a pressing portion 174. The needle member 170*c* is configured to break the partition wall portion 132 with the first needle member 170*c*1 and break the partition wall portion 132*a* with the second needle member 170*c*2.

The first needle member 170*c*1 has a sharp distal portion capable of breaking the partition wall portion 132, and the second needle member 170*c*2 has a sharp distal portion capable of breaking the partition wall portion 132*a*. The proximal portion of the first needle member 170*c*1 and the proximal portion of the second needle member 170*c*2 are attached to the pressing portion 174. Furthermore, the first needle member 170*c*1 and the second needle member 170*c*2 are attached to the pressing portion 174 at positions at which the first needle member 170*c*1 and the second needle member 170*c*2 intersect each other such that the partition wall portions 132 and 132*a* can be broken as illustrated in FIG. 8.

The pressing portion 174 is not particularly limited as long as it has a shape that can be easily pressed by the user such as the operator in the present modification example. For example, as illustrated in FIG. 8, the pressing portion 174 can be formed by a cylindrical member. However, the pressing portion 174 may be formed by a member (for example, a prismatic member or the like) other than the cylindrical shape. Furthermore, the surface of the pressing portion 174 on the pressing side may be a flat surface, but may be a curved surface other than the flat surface.

The treatment method using the medical elongated body set Sc according to the third modification example is different from the treatment method using the introducer sheath 100 according to the first embodiment in the operation of breaking the partition wall portion when the drug solution of the drug part is administered to the wound site P. In the third modification example, the operator inserts the needle member 170*c* into the support member 130*c* in a state in which the groove portion 112 of the catheter body 110 is inserted into or positioned in the wound site P. Specifically, in a state in which the groove portion 112 of the catheter body 110 is inserted into or positioned in the wound site P, the operator inserts the first needle member 170*c*1 and the second needle member 170*c*2 into the support member 130*c* with the marker portion 135 of the support member 130*c* as the mark in a state in which the needle member 170*c* is not inserted into or positioned in the support member 130*c* (see the needle member 170*c* indicated by a two-dot chain line in FIG. 8).

The operator breaks the partition wall portion 132 with the first needle member 170*c*1 and breaks the partition wall portion 132*a* with the second needle member 170*c*2 by inserting the needle member 170*c* into the support member 130*c*. Accordingly, the operator administers the drug solution of the drug part 131 and the drug solution of the drug part 131*a* to the wound site P via the groove portion 112. The other aspects of the treatment method are the same as described above with respect to the first embodiment, and so a detailed description of such aspects is not repeated.

As described above, the medical elongated body set Sc according to the third modification example includes the introducer sheath 100*c* and the needle member 170*c* having the sharp distal portion configured to break the partition wall portions 132 and 132*a*. The support member 130*c* includes a marker portion 135 serving as a mark when the needle member 170*c* is inserted in the circumferential direction of the catheter body 110. Therefore, even in a case where the needle member 170*c* is a member separate from the introducer sheath 100*c*, it is possible to break the partition wall portions 132 and 132*a* by inserting the needle member 170*c* with the marker portion 135 as a mark in a state in which the groove portion 112 of the catheter body 110 is inserted into or positioned in the wound site P, and to administer the drug solutions of the drug parts 131 and 131*a* to the wound site P via the groove portion 112.

Fourth Modification Example of First Embodiment

Figure 9:
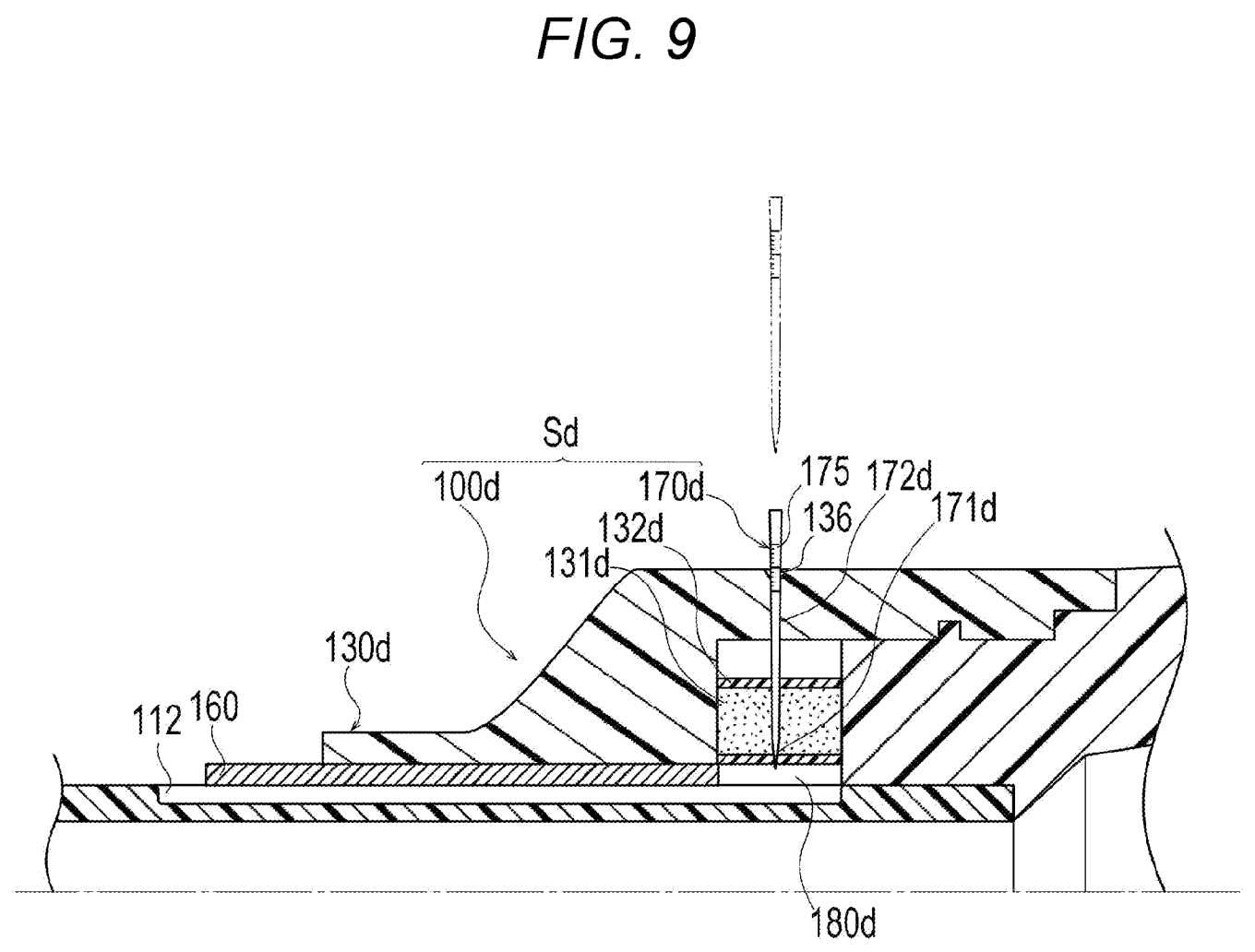

FIG. 9 is a view illustrating a medical elongated body set Sd according to the fourth modification example of the first embodiment and corresponds to the left side of the center line of FIG. 3. In the medical elongated body set Sd of the present fourth modification example, the introducer sheath 100*d* and a needle member 170*d* are separated from each other in an unused state as in the third modification example. That is, before use, the introducer sheath 100*d* is in a state in which the needle member 170 is not inserted into or positioned in the support member 130 in the introducer sheath 100 of the first embodiment. Furthermore, the medical elongated body set Sd is configured such that the position of the base portion 173 of the needle member 170*d* is located at the same position as a drug part 131*d* in the longitudinal direction of the catheter body 110 in a state in which the needle member 170*d* is inserted into or positioned in the drug part 131*d*. That is, the position of the base portion 173 of the needle member 170*d* overlaps the position of the drug part 131*d* in a radial direction of the catheter body.

The introducer sheath 100*d* has the same configuration as the introducer sheath 100*c* except for the drug part and the partition wall portion.

The drug part 131*d* is accommodated in the internal space of a support member 130*d* with a partition wall portion 132*d* in the present modification example. The partition wall portion 132*d* extends in the longitudinal direction of the catheter body 110. Furthermore, a space portion 180*d* is formed so as to be adjacent to the drug part 131*d* with the partition wall portion 132*d* interposed therebetween in the radial direction of the catheter body 110. With this configuration, when the operator inserts the needle member 170*d* into the partition wall portion 132*d*, it is possible to cause the drug solution of the drug part 131 to flow out to the groove portion 112. In the fourth modification example, as illustrated in FIG. 9, since the needle member 170*d* is a linear rod member, a marker portion 136 is provided at a position overlapping the position of the drug part 131*d* in the longitudinal direction of the catheter body 110. Other aspects of the marker portion 136 are similar to the aspects of the marker portion 135 of the third modification example, and so a detailed description of such aspects is not repeated.

In the fourth modification example, the operator inserts the needle member 170*d* into the same position as the drug part 131*d* in the longitudinal direction of the catheter body 110 of the support member 130*d*, and breaks the partition wall portion 132*d*.

As illustrated in FIG. 9, the needle member 170*d* has a distal portion 171*d*, a main body portion 172*d*, and a scale portion 175. The distal portion 171*d* of the needle member 170*d* has a sharp shape and is configured to be capable of breaking (i.e., is configured to break) the partition wall portion 132*d* by causing damage. The main body portion 172*d* of the needle member 170*d* is located on the proximal side of the distal portion 171*d* and can be gripped by the user such as the operator.

The scale portion 175 is provided on the main body portion 172*d* of the needle member 170*d*, and is configured such that the degree of insertion of the needle member 170*d* when the needle member 170*d* is inserted into or positioned in the support member 130*d* can be visually recognized. In a case where the operator forms a hole on the partition wall portion 132*d* with the needle member 170*d* and causes the drug solution of the drug part 131*d* to flow out to the space portion 180*d*, the operator needs to form the hole on the partition wall portion 132*d* by inserting the needle member 170*d* into the partition wall portion 132*d* and then withdrawing the needle member 170*d* from the partition wall portion 132*d*. Therefore, in the case of the fourth modification example of FIG. 9, after inserting the needle member 170*d* into the partition wall portion 132*d* on the catheter body 110 side, the operator needs to completely pull out the needle member 170*d* from the support member 130*d* or pull out the needle member 170*d* at least to the vicinity of the drug part 131*d* to cause the drug solution of the drug part 131*d* to flow out. The scale portion 175 can indicate an insertion limit when the needle member 170*d* is inserted to penetrate the partition wall portion 132*d* of the support member 130*d*. Accordingly, the scale portion 175 can prevent the operator from excessively inserting the needle member 170*d* and damaging the catheter body 110 when the operator inserts the needle member 170*d* into the support member 130*d*. Furthermore, when the operator pulls out the needle member 170*d* from the support member 130*d*, the scale portion 175 serves as a guide for the operator when the drug solution of the drug part 131*d* flows out. Therefore, the operator can administer the drug solution to the wound site P via the groove portion 112 without completely withdrawing the needle member 170*d* from the support member 130*d*. For example, the scale of the scale portion 175 can be provided at intervals of 1 mm. However, the specific configuration of the scale is not limited to the above-described scale as long as excessive insertion into the support member 130*d* can be suppressed.

In the treatment method using the medical elongated body set Sd according to the fourth modification example, the operation of breaking the partition wall portion 132*d* with the needle member 170*d* when the drug solution of the drug part is administered to the wound site P is different from that in the first embodiment. When inserting the needle member 170*d*, the operator inserts the needle member 170*d* into the support member 130*d* with the marker portion 136 as a mark in a state in which the groove portion 112 of the catheter body 110 is inserted into or positioned in the wound site P. Specifically, in a state in which the groove portion 112 of the catheter body 110 is inserted into or positioned in the wound site P, the operator uses the marker portion 136 of the support member 130*d*, which is located at the same position as the drug part 131*d* in the longitudinal direction of the catheter body 110, as a mark to insert the needle member 170*d* so as to penetrate the partition wall portion 132*d*. When inserting the needle member 170*d*, the operator performs an insertion operation while monitoring the scale portion 175 of the needle member 170*d*. Therefore, it is possible to prevent the needle member 170*d* from being excessively inserted into the catheter body 110.

Since the needle member 170*d* is inserted in a state in which the groove portion 112 of the catheter body 110 is inserted into or positioned in the puncture site and the partition wall portion 132*d* is broken, the drug solution of the drug part 131*d* can be administered to the wound site P via the groove portion 112.

As described above, in the fourth modification example, the needle member 170*d* is a separate member from the introducer sheath 100*d*, and the scale portion 175 is provided on the main body portion 172*d* of the needle member 170*d*. With this configuration, it is possible to prevent the needle member 170*d* from being excessively inserted into the catheter body 110 when the needle member 170*d* is inserted into the partition wall portion 132*d*.

Furthermore, similar to the third modification example, the medical elongated body set Sd of the fourth modification example includes the introducer sheath 100*d* and the needle member 170*d* having a sharp distal portion configured to break the partition wall portion 132*d*, and the support member 130*d* includes the marker portion 136 serving as a mark when the needle member 170*d* is inserted in the circumferential direction of the catheter body 110. Therefore, even in a case where the needle member 170*d* is a member separate from the introducer sheath 100*d*, it is possible to break the partition wall portion 132*d* by inserting the needle member 170*d* with the marker portion 136 as a mark in a state in which the groove portion 112 of the catheter body 110 is inserted into or positioned in the wound site P, and to administer the drug solution of the drug part 131*d* to the wound site P via the groove portion 112.

Fifth Modification Example of First Embodiment

Figure 10A:
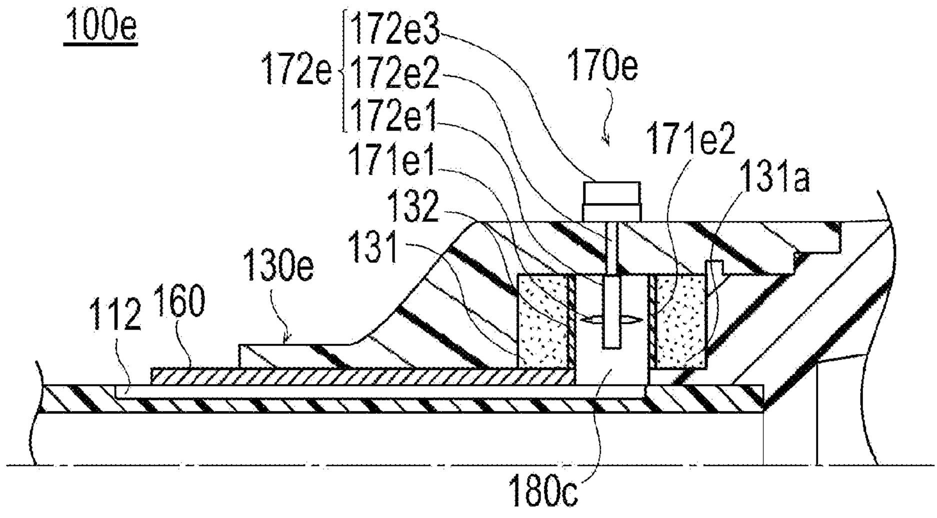
FIGS. 10A and 10B are modification examples of the support member and needle member.
Figure 10B:
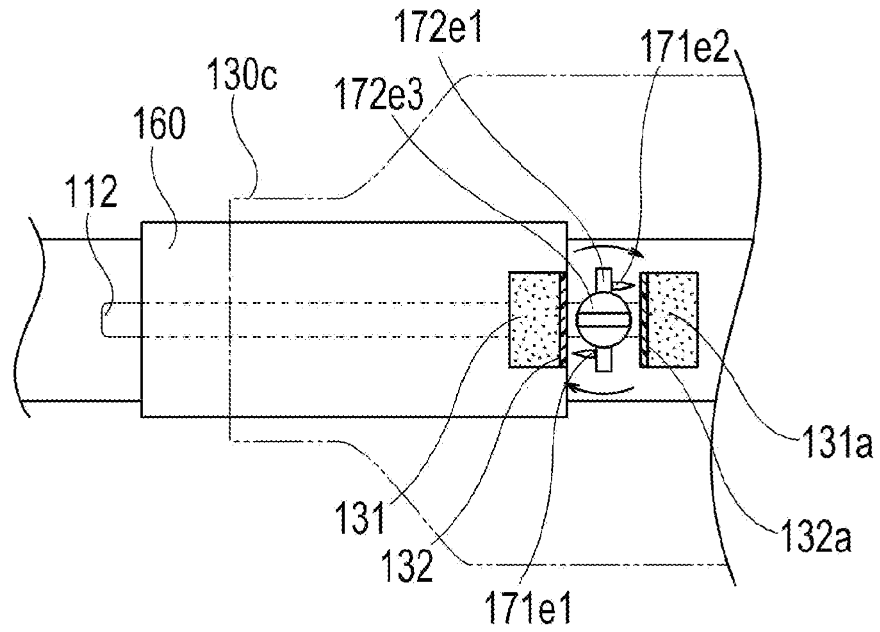

FIG. 10A is a view illustrating an introducer sheath 100*e* according to the fifth modification example of the first embodiment and corresponding to the left side of the center line of FIG. 3. FIG. 10B is a view illustrating a part of a support member 130*e* of the introducer sheath 100*e* of FIG. 10A according to the fifth modification example in a transparent manner, and is a view of the drug parts 131 and 131*a*, a needle member 170*e*, and the like when viewed from an outer side of the catheter body 110 in the radial direction.

As will be briefly described with reference to FIGS. 10A and 10B, in the fifth modification example, the needle member 170*e* is rotated with respect to the support member 130*e* to break the partition wall portions 132 and 132*a* and thus the drug solutions of the drug parts 131 and 131*a* is released into the groove portion 112. In the fifth modification example, the configuration of the needle member 170*e* is different from that of the needle member 170*c* according to the third modification example. The fifth modification example differs from the third modification example in that the needle member 170*e* is not configured separately from the introducer sheath, and the support member 130*e* is not provided with the marker portion 135 with respect to the support member 130*c* of FIG. 8. Other aspects of the fifth modification example are similar to the third modification example, and so a detailed description of the common or similar aspects configuration is not repeated.

As illustrated in FIGS. 10A and 10B, the needle member 170*e* according to the present modification example includes a first distal portion 171*e*1, a second distal portion 171*e*2, and a main body portion 172*e*. The main body portion 172*e* of the needle member 170*e* includes a rotation plate 172*e*1, a rotation shaft 172*e*2, and a grip portion 172*e*3.

The rotation plate 172*e*1 is formed by a plate-like member having a rectangular shape in plan view as illustrated in FIG. 10B. Specifically, the rotation plate 172*e*1 has a rectangular shape in plan view as illustrated in FIG. 10B. The first distal portion 171*e*1 is formed to be sharp so as to break the partition wall portion 132, and is provided on one surface of the rotation plate 172*e*1. The first distal portion 171*e*1 is provided on one surface of the rotation plate 172*e*1 and near an end of the rotation plate 172*e*1 in a width direction of the rotation plate 172*e*1 (vertical direction in FIG. 10B). The second distal portion 171*e*2 is formed to be sharp so as to break the partition wall portion 132*a*, and is provided on a surface opposite to the surface on which the first distal portion 171*e*1 of the rotation plate 172*e*1 is provided. The second distal portion 171*e*2 is provided on the rotation plate 172*e*1 and near an end located on the opposite side to the position at which the first distal portion 171*e*1 of the rotation plate 172*e*1 is provided in the width direction of the rotation plate 172*e*1. The first distal portion 171*e*1 and the second distal portion 171*e*2 are located in the space portion 180*c*.

The rotation shaft 172*e*2 is provided adjacent to the rotation plate 172*e*1, and is located on the outer side of the rotation plate 172*e*1 in the radial direction of the catheter body 110. When the operator rotates the rotation shaft 172*e*2, the rotation plate 172*e*1 rotates clockwise about the rotation shaft 172*e*2 as illustrated in FIG. 10B.

The grip portion 172*e*3 is provided adjacent to the rotation shaft 172*e*2, and is located on the outer side of the rotation shaft 172*e*2 in the radial direction of the catheter body 110. The grip portion 172*e*3 can be gripped by fingers of the user such as the operator. As illustrated in FIG. 10A, the grip portion 172*e*3 is located outside the support member 130*e*.

The partition wall portion of the support member 130*e* is provided at two positions, for example, the partition wall portion 132 and the partition wall portion 132*a* as in the third modification example of FIG. 8. When the operator rotates the rotation plate 172*e*1, the first distal portion 171*e*1 and the second distal portion 171*e*2 come into contact with the partition wall portion 132 and the partition wall portion 132*a* to break the partition wall portion 132 and the partition wall portion 132*a*. As illustrated in FIG. 10B, the partition wall portion 132 and the partition wall portion 132*a* do not come into contact with the first distal portion 171*e*1 and the second distal portion 171*e*2 when the end of the rotation plate 172*e*1 is at a position farthest from the partition wall portions 132 and 132*a*. On the other hand, when the operator rotates the rotation plate to move a position near the end of the rotation plate 172*e*1 in the rotation direction illustrated in FIG. 10B, the partition wall portion 132 and the partition wall portion 132*a* come into contact with the first distal portion 171*e*1 and the second distal portion 171*e*2 and are broken.

A treatment method using the introducer sheath 100*e* according to the fifth modification example is different from that of the first embodiment in the operation of breaking the partition wall portions 132 and 132*a* with the needle member 170*e* when the operator administers the drug solutions of the drug parts 131 and 131*a* to the wound site P. In the treatment method using the introducer sheath 100*e* according to the fifth modification example, the operator grips the grip portion 172*e*3 and rotates the rotation plate 172*e*1 about the rotation shaft 172*e*2 in a state in which the groove portion 112 of the catheter body 110 is inserted into or positioned in the wound site P. Specifically, as illustrated in FIGS. 10A and 10B, the operator grips the grip portion 172*e*3 and rotates the rotation plate 172*e*1 about the rotation shaft 172*e*2 in a state before the needle member 170*e* breaks the partition wall portions 132 and 132*a* (state in which the first distal portion 171*e*1 and second distal portion 171*e*2 of the rotation plate 172*e*1 do not come into contact with the partition wall portions 132 and 132*a*).

Accordingly, the first distal portion 171*e*1 comes into contact with the partition wall portion 132 and breaks the partition wall portion 132 by causing damage. Furthermore, the second distal portion 171*e*2 comes into contact with the partition wall portion 132*a* and breaks the partition wall portion 132*a* by causing damage. At this time, after the first distal portion 171*e*1 and the second distal portion 171*e*2 come into contact with the partition wall portions 132 and 132*a*, the operator returns the rotation plate 172*e*1 to the original position before the first distal portion 171*e*1 and the second distal portion 171*e*2 come into contact with the partition wall portions 132 and 132*a*, and thus can form holes on the partition wall portions 132 and 132*a*. Accordingly, the drug solutions of the drug parts 131 and 131*a* flow out from the holes (damaged portions) of the partition wall portions 132 and 132*a* to the space portion 180*c*, and are administered to the wound site P via the groove portion 112. Other aspects of the method of use of the fifth modification example are the same as the method of the first embodiment, and so a detailed description of such aspects is not repeated.

As described above, in the introducer sheath 100*e* according to the fifth modification example, the grip portion 172*e*3 of the needle member 170*e* is manipulated to rotate the rotation plate 172*e*1, the positions of the first distal portion 171*e*1 and second distal portion 171*e*2 of the needle member 170*e* is moved, and thus the partition wall portions 132 and 132*a* are broken. The needle member 170*e* includes the sharp first distal portion 171*e*1 and sharp second distal portion 171*e*2 configured to break the partition wall portions 132 and 132*a*, and the main body portion 172*e* extending from the first distal portion 171*e*1 and the second distal portion 171*e*2 toward the outside of the support member 130*e*. The grip portion 172*e*3, which is a part of the main body portion 172*e*, is located outside the support member 130*c*. With this configuration, the operator can manipulate the grip portion 172*e*3 located outside the support member 130*c* in a state in which the groove portion 112 of the catheter body 110 is inserted into or positioned in the wound site P, and can break the partition wall portions 132 and 132*a* with the first distal portion 171*e*1 and the second distal portion 171*e*2. Therefore, the operator can administer the drug solutions of the drug parts 131 and 131*a* to the wound site P. In the present modification example, it has been described that two drug parts and two partition wall portions are provided, but the number of drug parts and the number of partition wall portions are not limited to two as long as the partition wall portions can be broken by the rotation of the needle member to release the drug solutions of the drug parts.

Second Embodiment

Figure 11:
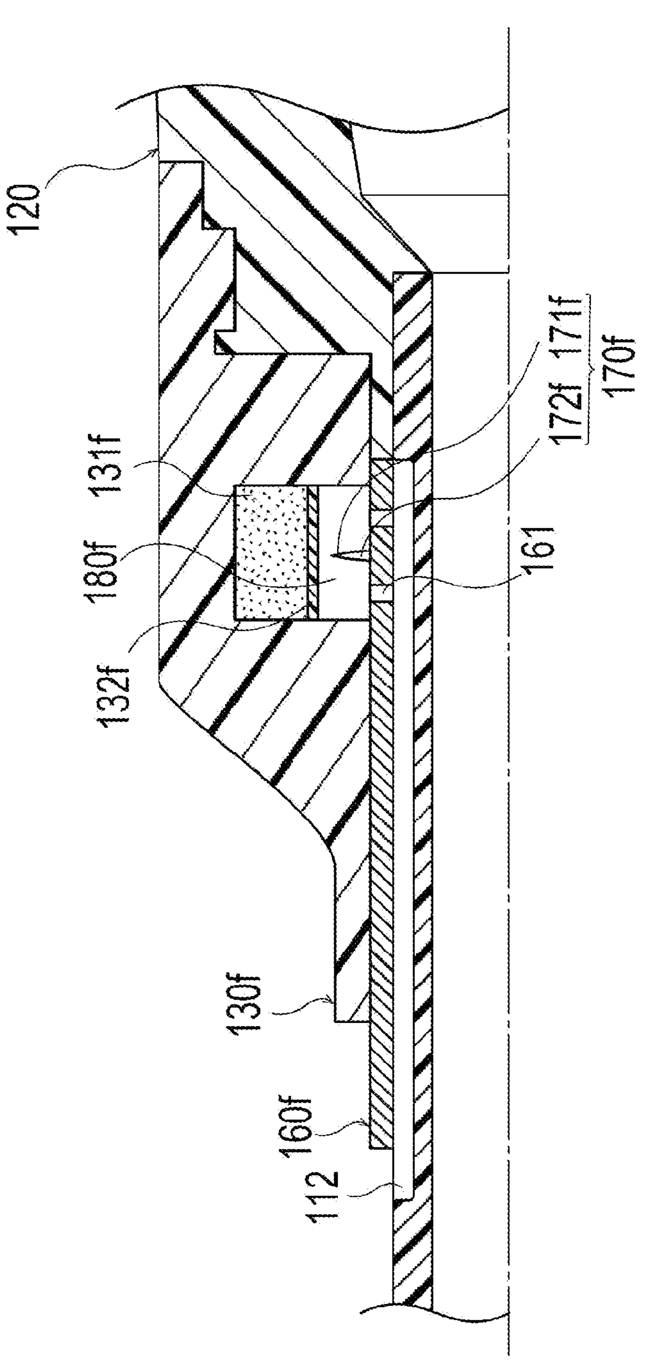
FIG. 11 is a view illustrating a portion of a medical elongated body according to a second embodiment, the portion corresponding to the left side of the center line of FIG. 3.

FIG. 11 is a view illustrating an introducer sheath 100*f* according to the second embodiment and corresponding to the left side of the center line of FIG. 3. When the second embodiment is briefly described with reference to FIG. 11, in the introducer sheath 100*f*, a cover member 160*f* is fixed to the hub 120. Furthermore, the cover member 160*f* includes a hole portion 161, and a main body portion 172*f* of a needle member 170*f* is fixed to the cover member 160*f*. In the second embodiment, the support member, the cover member, and the needle member are different from those of the first embodiment. Furthermore, the configurations of other features of the second embodiment are similar to features in the first embodiment, and so a detailed description of such common aspects of the second embodiment are not repeated.

A drug part 131*f* is made of the same material as that of the first embodiment, and is accommodated at a different position of a support member 130*f*. The drug part 131*f* is accommodated in the internal space of the support member 130*f* with a partition wall portion 132*f*. The drug part 131*f* is adjacent to the needle member 170*f* with the partition wall portion 132*f* interposed therebetween in the radial direction of the catheter body 110 (support member 130*f*). In the present embodiment, the drug part 131*f* is disposed on the outer side of the needle member 170*f* in the radial direction of the catheter body 110 (support member 130*f*).

The partition wall portion 132*f* is located on the catheter body side with respect to the drug part 131*f* in the internal space of the support member 130*f*, and extends in the longitudinal direction of the catheter body 110. Furthermore, as illustrated in FIG. 11, a space portion 180*f* is formed so as to be adjacent to the drug part 131*f* with the partition wall portion 132*f* interposed therebetween in the radial direction of the catheter body 110. Note that, in the support member 130*f*, a color different from the surrounding colors is applied only to the portion accommodating the drug part 131*f* such that the operator can easily recognize the position of the drug part 131*f*, and thus it is possible to prevent erroneous pressing of a different portion during the procedure.

Similar to the cover member 160, the cover member 160*f* is located (extends) from a position on the proximal side with respect to the distal end of the support member 130*f* to a position on the distal side with respect to the distal end of the support member 130*f* in the longitudinal direction of the catheter body 110. The cover member 160*f* is configured to cover at least a part of the groove portion 112, and the distal end of the cover member 160*f* is disposed so as to be located on the proximal side with respect to the distal end of the groove portion 112.

In the second embodiment, as illustrated in FIG. 11, the proximal portion of the cover member 160*f* is fixed to the hub 120. Furthermore, the cover member 160*f* is formed by a substantially cylindrical material as in the first embodiment, and includes the needle member 170*f*. The needle member 170*f* is fixed to the cover member 160*f*. Note that, as in the first embodiment, the cover member 160*f* is made of a metal material or a fluorine resin harder than the material of the catheter body 110 such that the outer diameter of the cover member 160*f* can be maintained and the cover member 160*f* can be smoothly inserted into the biological tissue when the catheter body 110 is inserted into the biological tissue.

Furthermore, in the second embodiment, as illustrated in FIG. 11, the cover member 160*f* is provided with the hole portion (through hole) 161 at a position connecting the groove portion 112 with the space portion 180*f* in the circumferential direction of the catheter body 110. Accordingly, when the operator breaks the partition wall portion 132*f* with the needle member 170*f*, the drug solution of the drug part 131*f* is released from the distal end of the groove portion 112 via the space portion 180*f*, the hole portion 161 of the cover member 160*f*, and the groove portion 112. Therefore, when the operator breaks the partition wall portion 132*f* in a state in which the groove portion 112 of the catheter body 110 is inserted into or positioned in the wound site P, the drug solution of the drug part 131*f* is administered to the wound site P via the groove portion 112. As illustrated in FIG. 11, it is preferable to provide a plurality of the hole portions (plural through holes) 161 in the cover member 160*f* such that the drug solution of the drug part 131*f* can efficiently flow out to the groove portion 112. The hole portion 161 may have a circular shape or other shapes. The specific number of the hole portions 161, and the specific shape of the hole portion(s) 161 are not limited to the number and the shape shown in FIG. 11 as long as the drug solution of the drug part 131*f* can be released to the wound site P via the groove portion 112.

The needle member 170*f* has a sharp distal portion 171*f* capable of breaking the partition wall portion 132*f*, and a main body portion 172*f* located on the proximal side with respect to the distal portion 171*f*. As illustrated in FIG. 11, the main body portion 172*f* of the needle member 170*f* is fixed to the cover member 160*f* such that the distal portion 171*f* of the needle member 170*f* faces the support member 130*f*.

A treatment method using the introducer sheath 100*f* according to the second embodiment is different from that of the first embodiment in the operation of breaking the partition wall portion 132*f* with the needle member 170*f* when the operator administers the drug solution of the drug part 131*f* to the wound site P. In the treatment method using the introducer sheath 100*f* according to the second embodiment, the operator presses the support member 130*f* toward the catheter body 110 in a state in which the groove portion 112 of the catheter body 110 is inserted into or positioned in the wound site P. At this time, the operator presses the outer surface of the support member 130*f* and makes the outer surface recessed such that the partition wall portion 132*f* comes into contact with the needle member 170*f* located in the cover member 160*f*. Accordingly, the needle member 170*f* approaches the partition wall portion 132*f*, and the distal portion 171*f* of the needle member 170*f* presses and breaks the partition wall portion 132*f*.

Accordingly, the drug solution of the drug part 131*f* is released to the space portion 180*f* and groove portion 112 via the hole portion 161 from the broken place of the partition wall portion 132*f*, and administered to the wound site P. Other features and aspects associated with this embodiment are the same as in the first embodiment, and so a detailed description of such aspects and features is not repeated.

As described above, in the second embodiment, the proximal portion of the cover member 160*f* is fixed to the hub 120, and the cover member 160*f* is provided with the hole portion 161 at a position connecting the groove portion 112 with the space portion 180*f* in the circumferential direction of the catheter body 110. In this manner, the proximal portion of the cover member 160*f* is fixed to the hub 120. Therefore, the cover member 160*f* of the second embodiment can prevent the movement (positional deviation) of the proximal portion of the cover member 160*f* when the operator places the cover member 160*f* in the biological tissue. Accordingly, the operator can smoothly insert the introducer sheath 100*f* into the blood vessel, and the operability of the operator is improved. Furthermore, the cover member 160*f* includes the hole portion 161. Therefore, in a state in which the groove portion 112 of the catheter body 110 is inserted into the wound site P, the operator can administer the drug solution of the drug part 131*f* to the wound site P via the hole portion 161 and the groove portion 112. Furthermore, in a case where the hub 120 is made of a material harder than the constituent material of the support member 130*f*, the proximal portion of the cover member 160*f* is fixed to the hub 120 harder than the support member 130*f*. Therefore, when the operator inserts the introducer sheath 100*f* into the blood vessel, the operator can more smoothly insert the cover member 160*f* into the blood vessel, and thus the operability of the operator is further improved.

Furthermore, the main body portion 172*f* of the needle member 170*f* is fixed to the cover member 160*f*. With such a configuration, in a state in which the groove portion 112 of the catheter body 110 is inserted into the wound site P, the operator can break the partition wall portion 132*f* with the distal portion 171*f* of the needle member 170*f* fixed to the cover member 160*f* and administer the drug solution of the drug part 131*f* to the wound site P. Therefore, the operator can break the partition wall portion 132*f* with the needle member 170*f* and administer the drug solution of the drug part 131*f* to the wound site P with a simple operation of pressing the outer surface of the support member 130*f*.

Modification Example of Second Embodiment

Figure 12:
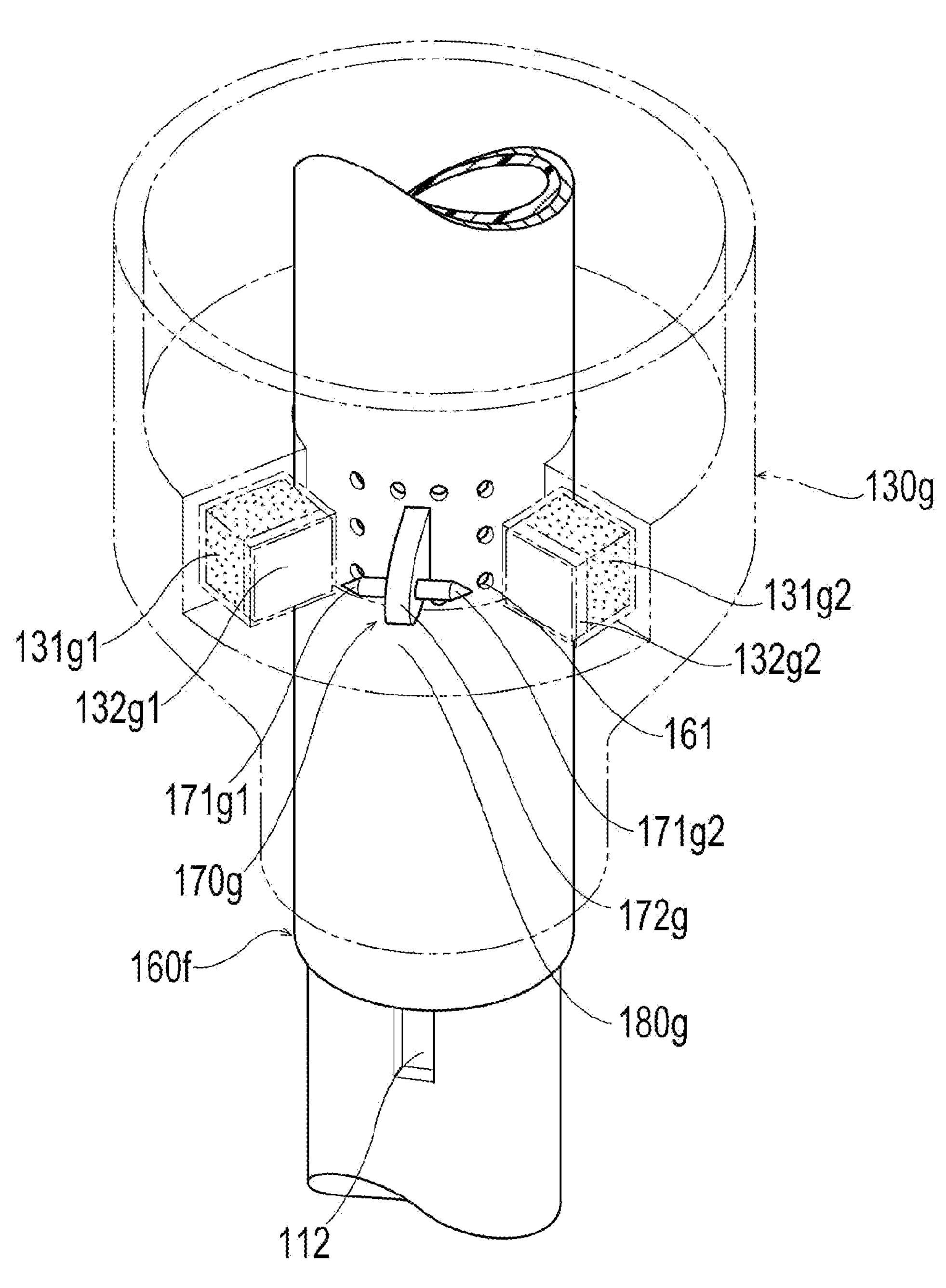
FIG. 12 is a perspective view illustrating a support member, a needle member, and a cover member in a medical elongated body according to a modification example of the second embodiment.
Figure 13:
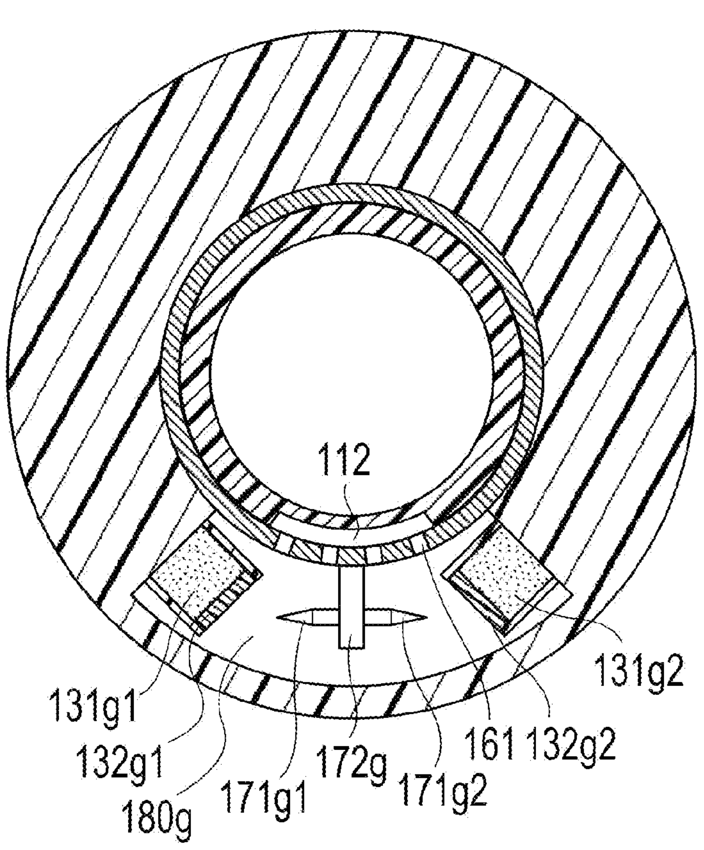
FIG. 13 is a cross-sectional view orthogonal to the longitudinal direction of the catheter body and illustrating a support member, a needle member, a cover member, a groove portion, and the like in the medical elongated body of FIG. 12.

FIG. 12 is a perspective view illustrating an introducer sheath 100*g* according to the modification example of the second embodiment, and FIG. 13 is a cross-sectional view taken in a direction orthogonal to the longitudinal direction of the catheter body 110 of FIG. 12, and is a view illustrating drug parts 131*g*1 and 131*g*2, partition wall portions 132*g*1 and 132*g*2, a needle member 170*g*, and a cover member 160*f*.

Describing the modification example of the second embodiment with reference to FIGS. 12 and 13, a first distal portion 171*g*1 of a needle member 170*g* faces the partition wall portion 132*g*1 in the circumferential direction of a support member 130*g*, and a second distal portion 171*g*2 faces the partition wall portion 132*g*2 in the circumferential direction of the support member 130*g*. The present modification example is different from the second embodiment in terms of the drug part, the partition wall portion, and the needle member. Other features of the present modification example are the same as in the second embodiment, and so a detailed description of such features is not repeated.

The support member 130*g* includes the drug part 131*g*1 and the drug part 131*g*2 at different positions in the circumferential direction of the support member 130*g*. The drug parts 131g1 and 131g2 are accommodated in the internal space of the support member 130g respectively with the partition wall portions 132g1 and 132g2.

As illustrated in FIG. 13, a space portion 180g is adjacent to the drug part 131g1 with the partition wall portion 132g1 interposed therebetween in the circumferential direction of the support member 130g. Furthermore, the space portion 180g is adjacent to the drug part 131g2 with the partition wall portion 132g2 interposed therebetween in the circumferential direction of the support member 130g. The space portion 180g is formed or positioned between the drug part 131g1 and the drug part 131g2 in the circumferential direction of the support member 130g.

Since the cover member 160f has the same configuration as that of the second embodiment, a detailed description is not repeated.

The needle member 170g has the sharp first distal portion 171g1 configured to break the partition wall portion 132g1, the sharp second distal portion 171g2 configured to break breaking the partition wall portion 132g2, and a main body portion 172g connecting the first distal portion 171g1 and the second distal portion 171g2 to the cover member 160f.

The first distal portion 171g1 is disposed so as to face the partition wall portion 132g1 in the circumferential direction of the support member 130g. The second distal portion 171g2 is disposed so as to face the partition wall portion 132g2 in the circumferential direction of the support member 130g.

The main body portion 172g is fixed to the cover member 160f. The main body portion 172g includes the first distal portion 171g1 on one side in the circumferential direction of the cover member 160f and the second distal portion 171g2 on the other side.

In a treatment method using the introducer sheath 100g according to the present modification example, it is different in that the operator breaks the partition wall portions 132g1 and 132g2 with the needle member 170g when administering the drug solution of the drug part to the wound site P. Specifically, the operator rotates the support member 130g in the circumferential direction of the catheter body 110 and the support member 130g in a state in which the groove portion 112 of the catheter body 110 is inserted into or positioned in the wound site P.

In a case where the operator rotates the support member 130g in the circumferential direction of the catheter body 110 and the support member 130g, when the support member 130g is rotated counterclockwise in FIG. 13, the first distal portion 171g1 of the needle member 170g comes into contact with the partition wall portion 132g1, and the partition wall portion 132g1 is broken due to damage. At this time, the drug solution of the drug part 131g1 is released from the broken place of the partition wall portion 132g1 and is administered to the wound site P via the hole portion 161 and the groove portion 112.

Furthermore, in a case where the operator rotates the support member 130g in the circumferential direction of the catheter body 110 and the support member 130g, when the support member 130g is rotated clockwise, the second distal portion 171g2 comes into contact with the partition wall portion 132g2, and the partition wall portion 132g2 is broken due to damage. At this time, similar to the drug part 131g1, the drug solution of the drug part 131g2 is released from the broken place of the partition wall portion 132g2 and is administered to the wound site P via the hole portion 161 and the groove portion 112. Other descriptions are similar, and thus the description thereof will be omitted.

As described above, in the present modification example, similar to the second embodiment, the main body portion 172g of the needle member 170g is fixed to the cover member 160f. With such a configuration, in a state in which the groove portion 112 of the catheter body 110 is inserted into the wound site P, the operator can break the partition wall portions 132g1 and 132g2 with the first distal portion 171g1 and second distal portion 171g2 of the needle member 170g of the main body portion 172g fixed to the cover member 160f and administer the drug solutions of the drug parts 131g1 and 131g2 to the wound site P via the hole portion 161 and the groove portion 112.

Figure 14:
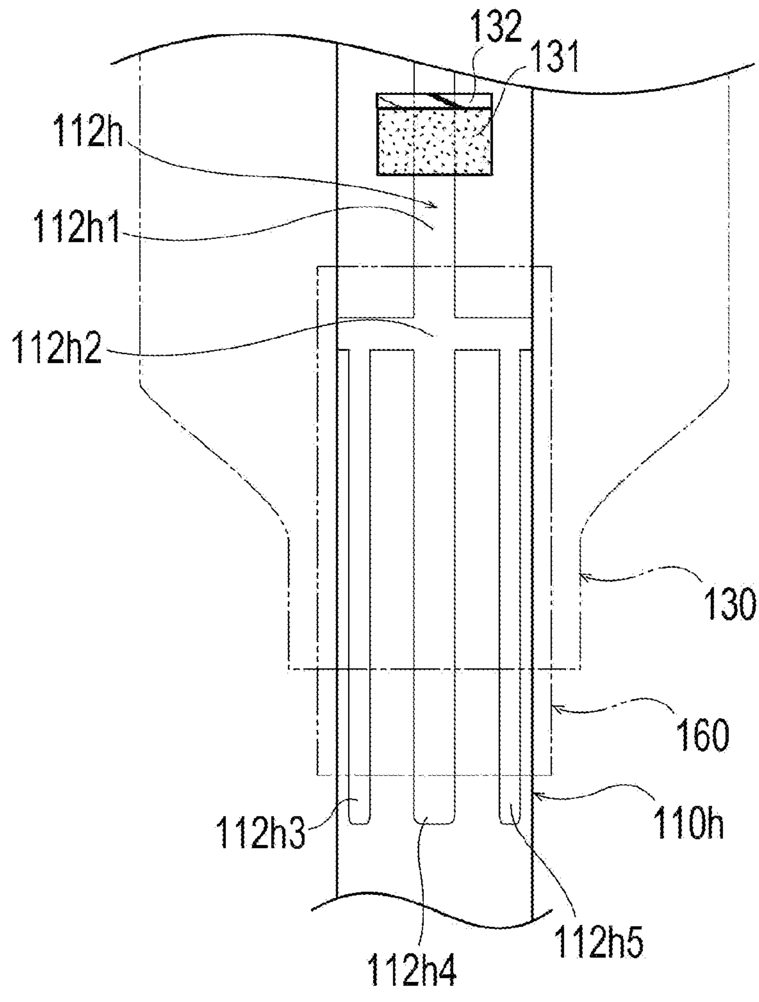
FIG. 14 is a view illustrating a modification example of a groove portion of the catheter body corresponding to the modification of FIGS. 10A and 10B.

The new medical elongate body disclosed here is not limited only to the above-described embodiments and modification examples, and various modifications can be made within the scope of the claims. FIG. 14 is a view illustrating a modification example of the fifth modification example of the first embodiment and a modification example of the groove portion of the catheter body. In the first embodiment, it has been described that the groove portion to which the drug solution flows out is provided at one position in the circumferential direction of the catheter body 110, but the medical elongate body is not limited thereto. For example, as illustrated in FIG. 14, the groove portion may be branched into a plurality of portions on the distal side of the catheter body 110.

As illustrated in FIG. 14, a groove portion 112h may include a first portion 112h1 extending from the drug part 131 toward the distal side of a catheter body 110h, a second portion 112h2 extending from the distal end of the first portion 112h1 in the circumferential direction of the catheter body 110h, and third portions 112h3, 112h4, and 112h5 branching from the second portion 112h2 and extending toward the distal side of the catheter body 110h in the longitudinal direction of the catheter body 110h, other than the case where the groove portion is provided at one position in the circumferential direction of the catheter body. It is preferable that the second portion 112h2 is located at a position on the proximal side with respect to the distal end of the cover member 160. Accordingly, since the second portion 112h2 extending in the circumferential direction of the catheter body 110h is not exposed on the distal side with respect to the distal end of the cover member 160, the catheter body 110h is configured to suppress kinking with the second portion 112h2 as a starting point. For these reasons, it is preferable that the second portion 112h2 is not exposed from the cover member 160 from the viewpoint of the insertability of the medical elongated body. Furthermore, although the third portion is provided at three positions in FIG. 14, the specific number of third portions may be other than three.

With such a configuration, in a state in which the groove portion 112 of the catheter body 110 is inserted into the wound site P, the operator can cause the drug solution of the drug part 131 to flow out in a wide range in the circumferential direction of the catheter body 110, and administer the drug solution to the wound site P.

Furthermore, it has been described that in the introducer sheaths of the first embodiment, the first modification example, the second modification example, the third modification example, the fourth modification example, and the fifth modification example, the cover member is fixed to the support member, and in the introducer sheaths of the second embodiment and the modification example, the cover member is fixed to the hub. However, in a case where the introducer sheath is configured such that the drug part and the groove portion are communicable with each other in a state in which the partition wall portion is broken by the needle member, instead of fixing the cover member to the support member as in the first embodiment, the first modification example, the second modification example, the third modification example, the fourth modification example, and the fifth modification example, the cover member provided with the hole portion is fixed to the hub. Furthermore, in a case where the introducer sheath is configured such that the drug part and the groove portion is communicable with each other in a state in which the partition wall portion is broken by the needle member, instead of fixing the cover member provided with the hole portion to the hub as in the second embodiment and the modification example, the cover member may be fixed to the support member as in the first embodiment.

The detailed description above describes embodiments of a medical elongated body, medical elongated body set and method of treatment representing examples of the new medical elongate body, medical elongated body set and treatment method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents that fall within the scope of the claims are embraced by the claims.

What is claimed is:

1. A medical elongated body comprising:

a catheter body, the catheter body possessing a proximal portion and an outer surface;

a hub fixed to the proximal portion of the catheter body;

a support member connected to the hub and covering a part of a proximal side of the catheter body, the catheter body including a groove on the outer surface of the catheter body;

the support member partially covering the groove;

the support member including a drug part having a drug solution, and a partition wall portion located between the drug part and the groove; and the partition wall portion being breakable by pressure or by causing damage to communicate the drug part with the groove.

2. The medical elongated body according to claim 1, further comprising:

a needle having a sharp distal portion positioned to contact and break the partition wall portion to communicate the drug part with the groove, the needle including a distal portion; and a space adjacent to the drug part, the partition wall portion being interposed between the catheter body and the support member, the distal portion of the needle being located in the space.

3. The medical elongated body according to claim 2, wherein the needle also includes a main body portion located proximal of the distal portion, and a part of the main body portion of the needle being located outside the support member.

4. The medical elongated body according to claim 3, wherein the needle has a base portion located outside the support member, and the base portion is located at a position different from the drug part in a longitudinal direction of the catheter body.

5. The medical elongated body according to claim 3, wherein the support member includes a convex portion that covers the main body portion located outside the support member.

6. The medical elongated body according to claim 1, further comprising a cover member extending in a longitudinal direction of the catheter body from a position proximal of a distal end of the support member to a position distal of the distal end of the support member, wherein the cover member covers at least a part of the groove, and a distal end of the cover member is proximal of a distal end of the groove.

7. The medical elongated body according to claim 3, further comprising a cover member extending in a longitudinal direction of the catheter body from a position a proximal of a distal end of the support member to a position distal of the distal end of the support member, wherein a part of the cover member covers at least a portion of the groove, and a distal end of the cover member is located on proximal of a distal end of the groove, a proximal portion of the cover member is fixed to the hub, and the cover member includes a through hole communicating the groove with the space in a circumferential direction of the catheter body.

8. The medical elongated body according to claim 7, wherein the main body portion of the needle is fixed to the cover member.

9. A medical elongated body set comprising:

the medical elongated body according to claim 1;

a needle having a sharp distal portion configured to break the partition wall portion; and the support member including a marker identifying a location, in a circumferential direction of the catheter body, at which the needle is to be inserted into the support member.

10. A medical elongated body comprising:

an elongated catheter body extending in a longitudinal direction from a proximal end of the elongated catheter body to a distal end of the elongated catheter body, the elongated catheter body possessing a proximal portion positioned closer to the proximal end of the elongated catheter body than the distal end of the elongated catheter body, the elongated catheter body also possessing an outer surface;

a hub fixed to the proximal portion of the elongated catheter body, the hub possessing a proximal end and a distal end;

a support member connected to the hub, the support member surrounding a portion of the elongated catheter body located distal of the distal end of the hub, the support member possessing an outer surface;

the elongated catheter body including a groove on the outer surface of the elongated catheter body, an axially extending portion of the support member overlying one portion of the groove, an other portion of the groove being uncovered and exposed to outside the elongated catheter body, the other portion of the groove being distal of the one portion of the groove;

a drug solution contained in an enclosed part that is located radially inwardly of the outer surface of the support member and radially outwardly of the outer surface of the elongated catheter body, the enclosed part including a partition wall, the enclosed part enclosing the drug solution in a way that prevents the drug solution from flowing into the groove; and the partition wall portion being breakable by contact with an object so that the drug solution in the enclosed part is free to flow to the groove.

11. The medical elongated body according to claim 10, wherein the partition wall includes first and second oppositely facing surfaces, the first surface facing the enclosed part and the second surface facing a space that communicates with the groove, the drug solution flowing from the enclosed part to the space and from the space to the groove upon breaking the partition wall.

12. The medical elongated body according to claim 10, further comprising a cover member that borders a part of the enclosed part, the cover member surrounding a part of the outer surface of the elongated catheter body and overlying a part of the groove, the cover member extending in the longitudinal direction from a proximal end of the cover member to a distal end of the cover member, the groove extending distally beyond the distal end of the cover member so that a distal portion of the groove is exposed.

13. The medical elongated body according to claim 10, further comprising a cover member that borders a part of the enclosed part, the cover member surrounding a part of the outer surface of the elongated catheter body and overlying a part of the groove, the cover member extending in the longitudinal direction from a proximal end of the cover member to a distal end of the cover member, the groove including a distal end portion and a proximal end portion, the distal end portion of the groove extending distally beyond the distal end of the cover member and the proximal end portion of the groove extending proximally beyond the proximal end of the cover member, so that both the extending distally beyond the distal end of the cover member so that a distal portion of the groove is exposed.

14. The medical elongated body according to claim 13, wherein the partition wall includes first and second oppositely facing surfaces, the first surface of the partition wall facing the enclosed part and the second surface of the partition wall facing a space that communicates with the proximal end portion of the groove.

15. The medical elongated body according to claim 10, wherein the enclosed part is a first enclosed part, the partition wall is a first partition wall and the drug solution is a first amount of the drug solution, and further comprising a second enclosed part containing a second amount of the drug solution, the second enclosed part being located radially inwardly of the outer surface of the support member and radially outwardly of the outer surface of the elongated catheter body, the first and second enclosed parts being spaced apart from one another so that a space exists between the first and second enclosed parts, the space being in communication with the groove, the second enclosed part including a second partition plate that is breakable so that the second amount of the drug solution in the second enclosed part is free to flow from the second enclosed part to the space and from the space to the groove.

16. The medical elongated body according to claim 15, wherein the first and second enclosed parts are axially spaced apart from one another so that the second enclosed part is proximal of the first enclosed part.

17. The medical elongated body according to claim 15, wherein the first and second enclosed parts are circumferentially spaced apart from one another.

18. The medical elongated body according to claim 10, further comprising a needle movably mounted in the support member so that the needle is movable relative to the support member, the needle possessing a central axis that intersects the partition wall, the needle including a sharp distal portion positioned to contact and break the partition wall when the needle is moved in a forward direction relative to the support member, the needle also including a base portion at a proximal end of the needle, the base end being positioned outside the support member.

19. The medical elongated body according to claim 10, wherein the groove includes an axially extending first groove portion that communicates with a circumferentially extending second groove portion, the circumferentially extending second groove portion extending circumferentially about a portion of a circumferential extent of the outer surface of the elongated catheter body, the circumferentially extending second groove portion communicating with a plurality of axially extending third groove portions that are positioned distal of the first groove portion.

20. A treatment method comprising:

percutaneously inserting a medical elongated body through a wound site and into a biological lumen, the medical elongated body comprising: a catheter body extending in a longitudinal direction and possessing a proximal portion and an outer surface, the catheter body including a groove on the outer surface of the catheter body; a hub fixed to the proximal portion of the catheter body; a support member connected to the hub and covering a part of the catheter body, the support member also covering a part of the groove, the support member possessing a distal end and a proximal end; a drug solution in an enclosed part that prevents the drug solution in the enclosed part from flowing into the groove, the enclosed part being positioned radially inwardly of an outer surface of the support member and being positioned between the proximal and distal ends of the support member relative to the longitudinal direction, the enclosed part including a partition wall;

positioning the medical elongated body so that a portion of the groove faces the wound site; and breaking the partition wall so that the drug solution flows into the groove and is brought into contact with the wound site by way of the portion of the groove facing the wound site.

* * * * *